US011649434B2

(12) United States Patent
Spence et al.

(10) Patent No.: US 11,649,434 B2
(45) Date of Patent: May 16, 2023

(54) COMPOSITIONS AND METHODS FOR OBTAINING FUNCTIONAL BASAL-LIKE CELLS

(71) Applicant: The Regents of the University of Michigan, Ann Arbor, MI (US)

(72) Inventors: Jason Spence, Ann Arbor, MI (US); Alyssa Miller, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 777 days.

(21) Appl. No.: 16/678,521

(22) Filed: Nov. 8, 2019

(65) Prior Publication Data

US 2020/0149004 A1 May 14, 2020

Related U.S. Application Data

(60) Provisional application No. 62/757,553, filed on Nov. 8, 2018.

(51) Int. Cl.
*C12N 5/071* (2010.01)

(52) U.S. Cl.
CPC ......... *C12N 5/0625* (2013.01); *C12N 5/0688* (2013.01); *C12N 2501/119* (2013.01); *C12N 2501/15* (2013.01); *C12N 2501/155* (2013.01); *C12N 2501/415* (2013.01); *C12N 2501/727* (2013.01); *C12N 2501/999* (2013.01); *C12N 2506/02* (2013.01); *C12N 2506/27* (2013.01); *C12N 2506/45* (2013.01)

(58) Field of Classification Search
None
See application file for complete search history.

(56) References Cited

U.S. PATENT DOCUMENTS

2021/0115408 A1\* 4/2021 Snoeck ................ C12N 5/0689

OTHER PUBLICATIONS

Butler et al, Am J Respiratory and Critical Care Medicine, 2016, vol. 194, No. 2, pp. 156-168. (Year: 2016).\*
Kodaira et al, Biochemical and Biophysical Research Communications, 2006, 345: 1224-1231. (Year: 2006).\*
ThermoFisher Scientific, Application Note: S0801 "Growth Factors in Thermo Scientific HyClone Cell Culture Serum" (2007) retrieved from URL https://static.thermoscientific.com/images/D22225~.pdf on Aug. 15, 2022. (Year: 2007).\*
Smirnova et al, Respiratory Research, 2016, vol. 17:83 (11 pages) (Year: 2016).\*
Abler LL, et al., "Conditional Gene Inactivation Reveals Roles for Fgf10 and Fgfr2 in Establishing a Normal Pattern of Epithelial Branching in the Mouse Lung" Dev. Dyn. Aug. 2009;238(8):1999-2013.
Agha, et al., "Fgf10-positive cells represent a progenitor cell population during lung development and postnatally" Development. 2014, 141, 296-306.
Andrews et al., "Embryonic stem (ES) cells and embryonal carcinoma (EC) cells: opposite sides of the same coin." 2005, Biochem Soc Trans 33:1526-1530.
Ang SL, et al., "HNF-3 beta is essential for node and notochord formation in mouse development." Cell. Aug. 26, 1994;78(4):561-74.
Balasooriya, GI, et al., FGFR2 is required for airway basal cell self-renewal and terminal differentiation. Development. May 1, 2017;144(9):1600-1606.
Bellusci S, et al., "Involvement of Sonic hedgehog (Shh) in mouse embryonic lung growth and morphogenesis." Development. Jan. 1997;124(1):53-63.
Boers JE, et al., "Number and proliferation of basal and parabasal cells in normal human airway epithelium." American Journal of Respiratory and Critical Care Medicine. Jun. 1998;157(6 Pt 1):2000-6.
Booth AJ, et al., "Acellular normal and fibrotic human lung matrices as a culture system for in vitro investigation." American Journal of Respiratory and Critical Care Medicine. Nov. 1, 2012;186(9):866-76.
Bort, et al., "Hex homeobox gene-dependent tissue positioning is required for organogenesis of the ventral pancreas." Development, 2004, 131(4),797-80.
Boucherat O, et al., "Decreased Lung Fibroblast Growth Factor 18 and Elastin in Human Congenital Diaphragmatic Hernia and Animal Models" American Journal of Respiratory and Critical Care Medicine. May 15, 2007;175(10):1066-77.
Carre A, et al., "Five new TTF1/NKX2.1 mutations in brain-lung-thyroid syndrome: rescue by PAX8 synergism in one case." Hum. Mol. Genet. Jun. 15, 2009;18(12):2266-76.
Chambers SM, et al., "Highly efficient neural conversion of human ES and iPS cells by dual inhibition of SMAD signaling." Nat Biotechnol. Mar. 1, 2009;27(3):275-80.
Chang DR, et al., "Evening use of light-emitting eReaders negatively affects sleep, circadian timing, and next-morning alertness" Proceedings of the National Academy of Sciences. Sep. 20, 2013, 1232-1237.
Chen L, et al., "Dynamic Regulation of Platelet-Derived Growth Factor Receptor α Expression in Alveolar Fibroblasts during Realveolarization. American Journal of Respiratory Cell and Molecular Biology." American Journal of Respiratory Cell and Molecular Biology. Oct. 2012;47(4):517-27.

(Continued)

*Primary Examiner* — Allison M Fox
(74) *Attorney, Agent, or Firm* — Casimir Jones, SC; Robert A. Goetz

(57) ABSTRACT

The invention disclosed herein generally relates to methods and systems for converting stem cells into specific tissue(s) or cells through directed differentiation. In particular, the invention disclosed herein relates to methods and systems for promoting functional basal-like cells from pluripotent stem cell-derived lung bud tip progenitor organoid tissue through activation of SMAD signaling via activation of TGFβ1 (and/or the TGFβ signaling pathway) and BMP4 (and/or the BMP signaling pathway).

1 Claim, 15 Drawing Sheets

(56) References Cited

OTHER PUBLICATIONS

Chen Y-J, et al., "De Novo Formation of Insulin-Producing "Neo-B Cell Islets" from Intestinal Crypts" Cell Rep.; Mar. 4, 2014;:1-13.
D'Amour KA, et al., "Efficient differentiation of human embryonic stem cells to definitive endoderm." Nat Biotechnol. Oct. 28, 2005;23(12):1534-41.
D'Amour KA, et al., "Production of pancreatic hormone-expressing endocrine cells from human embryonic stem cells." Nat Biotechnol. Nov. 2006;24(11):1392-401.
Danopoulous, S, et al. Human lung branching morphogenesis is orchestrated by the spatiotemporal distribution of ACTA2, SOX2, and SOX9. Am J Physiol Lung Cell Mol Physiol. Jan. 1, 2018;314(1):L144-L149.
Delaforest A, et al., "HNF4A is essential for specification of hepatic progenitors from human pluripotent stem cells." Development. Oct. 2011;138(19):4143-53.
Desai TJ, et al., "Reconstructing lineage hierarchies of distal lung epithelium using single-cell RNA-seq" Nature. Feb. 5, 2014; Treutlein B, et al., Nature. May 15, 2014;509(7500):371-5.
Domyan ET, et al., "Signaling through BMP receptors promotes respiratory identity in the foregut via repression of Sox2" Development. Feb. 8, 2011;138(5):971-81.
Eisen, et al., "Cluster analysis and display of genome-wide expression patterns" PNAS Dec. 8, 1998 vol. 95 No. 25 14863-14868.
Evans and Kaufman, "Establishment in culture of pluripotential cells from mouse embryos." 1981, Nature 292(5819): 154-156.
Evans MJ, et al., "Cellular and molecular characteristics of basal cells in airway epithelium." Exp. Lung Res. Jul. 2001;27(5):401-15.
Firth AL, et al., "Generation of multiciliated cells in functional airway epithelia from human induced pluripotent stem cells" Proceedings of the National Academy of Sciences. Apr. 29, 2014;111(17):E1723-30.
Ghaedi M, et al., "Human iPS cell-derived alveolar epithelium repopulates lung extracellular matrix." J. Clin. Invest. Nov. 1, 2013;123(11):4950-62.
Green MD, et al., "Generation of anterior foregut endoderm from human embryonic and induced pluripotent stem cells" Nat Biotechnol. Nature Publishing Group; Feb. 27, 2011:1-7.
Hebrok M, et al., "Notochord repression of endodermal Sonic hedgehog permits pancreas development." Genes & Development. Jun. 1, 1998;12(11):1705-13.
Hinz B, et al., "The myofibroblast: one function, multiple origins." The American Journal of Pathology. Jun. 2007;170(6):1807-16.
Hong,et al., Basal cells are a multipotent progenitor capable of renewing the bronchial epithelium. Am J Pathol. Feb. 2004;164(2):577-88.
Huang SXL, et al., "Efficient generation of lung and airway epithelial cells from human pluripotent stem cells" Nat Biotechnol; 2014; 32(1), 84-94.
Jiang D., et al., "Cluster Analysis for Gene Expression Data: A Survey" IEEE Trans. Knowl. Data Eng. Nov. 2004;16(11):1370-86.
Kadzik RS, et al., "Directing lung endoderm differentiation in pluripotent stem cells." Cell Stem Cell. Apr. 6, 2012;10(4):355-61.
Kaji et al., 2009, "Virus-free induction of pluripotency and subsequent excision of reprogramming factors." Nature 458:771-775.
Kimura S, et al., "The T/ebp null mouse: thyroid-specific enhancer-binding protein is essential for the organogenesis of the thyroid, lung, ventral forebrain, and pituitary" Genes Dev. Jan. 1;10(1):60-927.
Kimura, et al., The T/ebp null mouse: thyroid-specific enhancer-binding protein is essential for the organogenesis of the thyroid, lung, ventral forebrain, and pituitary. Genes Dev. Jan. 1, 1996;10(1):60-9.
Klimanskaya et al., "Human embryonic stem cells derived without feeder cells" 2005, Lancet 365 (9471): 1636-1641.
Ko L., et al., "Alpha smooth muscle actin expression in developing and adult human lung." Differentiation. Aug. 1990;44(2):143-9.
Kroon E, et al., "Pancreatic endoderm derived from human embryonic stem cells generates glucose-responsive insulin-secreting cells in vivo." Nat Biotechnol. Feb. 20, 2008;26(4):443-52.

Kumar and Melton, "Pancreas specification: a budding question" Curr. Opin. Genet. Dev., 2003, 13,401-407.
Kuo, et al., "GATA4 transcription factor is required for ventral morphogenesis and heart tube formation." Genes Dev. 1997, 11,1048-1060.
Kusakabe T, et al., "Thyroid-specific enhancer-binding protein/NKX2.1 is required for the maintenance of ordered architecture and function of the differentiated thyroid." Mol. Endocrinol. 2006 g;20(8):1796-809.
Lancaster MA, et al., "Cerebral organoids model human brain development and microcephaly." Nature. Sep. 2013;501(7467):373-9.
Li Y, et al., "Sonic hedgehog signaling regulates Gli3 processing, mesenchymal proliferation, and differentiation during mouse lung organogenesis" Developmental Biology. Jun. 1, 2004;270(1):214-31.
Loh KM, et al., "Efficient endoderm induction from human pluripotent stem cells by logically directing signals controlling lineage bifurcations." Cell Stem Cell. Feb. 6, 2014;14(2):237-52.
Longmire TA, et al., "Efficient derivation of purified lung and thyroid progenitors from embryonic stem cells." Cell Stem Cell. Apr. 6, 2012;10(4):398-411.
Low RB, et al., "Lung smooth muscle differentiation." Int. J. Biochem. Cell Biol. Aug. 1998;30(8):869-83.
Mansouri A, et al., "Follicular cells of the thyroid gland require Pax8 gene function." Nat Genet. May 1998;19(1):87-90.
Martin "Teratocarcinomas and mammalian embryogenesis." 1980, Science 209 (4458):768-776.
Martinez Barbera, et al., "The homeobox gene Hex is required in definitive endodermal tissues for normal forebrain, liver and thyroid formation." Development, 2000, 127,2433-2445.
McCracken KW, et al., "Generating human intestinal tissue from pluripotent stem cells in vitro. Nature Protocols." Nature Protocols; Nov. 10, 2011;6(12):1920-8.
McCracken KW, et al., "Modelling human development and disease in pluripotent stem-cell-derived gastric organoids" Nature; Oct. 29, 2014;:1-19; 7.
Meyer JS, et al., "Optic vesicle-like structures derived from human pluripotent stem cells facilitate a customized approach to retinal disease treatment." Stem Cells. Aug. 2011;29(8):1206-18.
Miller, AJ, et al. In Vitro Induction and In Vivo Engraftment of Lung Bud Tip Progenitor Cells Derived from Human Pluripotent Stem Cells. Stem Cell Reports. Jan. 9, 2018;10(1):101-119.
Min H, et al., "Fgf-10 is required for both limb and lung development and exhibits striking functional similarity to *Drosophila* branchless." Genes & Development. Oct. 15, 1998;12(20):3156-61.
Monaghan AP, et al., "Postimplantation expression patterns indicate a role for the mouse forkhead/HNF-3 alpha, beta and gamma genes in determination of the definitive endoderm, chordamesoderm and neuroectoderm." Development. Nov. 1993;119(3):567-78.
Morrisey EE, et al., "Preparing for the first breath: genetic and cellular mechanisms in lung development." Developmental Cell.; Jan. 19, 2010;18(1):8-23.
Morrisey, et al., "GATA6 regulates HNF4 and is required for differentiation of visceral endoderm in the mouse embryo" Genes Dev., 1998, 12,3579-3590.
Motoyama J, et al., "Essential function of Gli2 and Gli3 in the formation of lung, trachea and oesophagus." Nat Genet. Sep. 1998;20(1):54-7.
Mou H, et al., "Generation of multipotent lung and airway progenitors from mouse ESCs and patient-specific cystic fibrosis iPSCs." Cell Stem Cell. Apr. 6, 2012;10(4):385-97.
Mou, H, et al. Dual SMAD Signaling Inhibition Enables Long-Term Expansion of Diverse Epithelial Basal Cells. Cell Stem Cell, 2016; 19(2): 217-231.
Nakajima M, et al., "Immunohistochemical and ultrastructural studies of basal cells, Clara cells and bronchiolar cuboidal cells in normal human airways" Pathol. Int. Dec. 1998;48(12):944-53.
Nakano T, et al., "Self-formation of optic cups and storable stratified neural retina from human ESCs." Cell Stem Cell. Jun. 14, 2012;10(6):771-85.

(56) References Cited

OTHER PUBLICATIONS

Narumi S, et al., "Functional characterization of four novel PAX8 mutations causing congenital hypothyroidism: new evidence for haploinsufficiency as a disease mechanism." Eur. J. Endocrinol. Nov. 2012;167(5):625-32.
Nikolic, MZ, et al. Human embryonic lung epithelial tips are multipotent progenitors that can be expanded in vitro as long-term selfrenewing organoids. Elife. Jun. 30, 2017;6. pii: e26575.
Offield, et al., PDX-1 is required for pancreatic outgrowth and differentiation of the rostral duodenum. Development. Mar. 1996;122(3):983-95.
Okita et al., "Generation of mouse induced pluripotent stem cells without viral vectors." 2008, Science 322(5903):949-953.
Okubo T; "Nmyc plays an essential role during lung development as a dosage-sensitive regulator of progenitor cell proliferation and differentiation" Development. Feb. 9, 2005;132(6):1363-74.
Prasov L, et al., "Math5 (Atoh7) gene dosage limits retinal ganglion cell genesis." Neuroreport. Jul. 11, 2012;23(10):631-4.
Rankin SA, Zorn AM. "Gene Regulatory Networks Governing Lung Specification." J Cell Biochem. Aug. 2014;115(8):1343-50.
Rawlins EL, et al., "The Id2+ distal tip lung epithelium contains individual multipotent embryonic progenitor cells." Development. Nov. 2009;136(22):3741-5.
Ringner M.; "What is principal component analysis?" Nat Biotechnol. Mar. 2008;26(3):303-4.
Rock JR, et al., "Basal cells as stem cells of the mouse trachea and human airway epithelium." Proceedings of the National Academy of Sciences. Aug. 4, 2009;106(31):12771-5.
Rockich BE, et al., "Sox9 plays multiple roles in the lung epithelium during branching morphogenesis" Proceedings of the National Academy of Sciences. Nov. 4, 2013, E4456-E4464.
Rossant, et al., "Expression of a retinoic acid response element-hsplacZ transgene defines specific domains of transcriptional activity during mouse embryogenesis." Genes Dev., 1991 5,1333-1344.
Schmitz G, et al., "Structure and function of lamellar bodies, lipid-protein complexes involved in storage and secretion of cellular lipids." J. Lipid Res. Oct. 1991;32(10):1539-70.
Serls AE.; "Different thresholds of fibroblast growth factors pattern the ventral foregut into liver and lung." Development. Dec. 2, 2004;132(1):35-47.
Si-Tayeb K, et al., "Highly efficient generation of human hepatocyte-like cells from induced pluripotent stem cells." Hepatology. Oct. 1, 2010;51(1):297-305.
Spence JR, et al., "Directed differentiation of human pluripotent stem cells into intestinal tissue in vitro." Nature. Feb. 3, 2011;470(7332):105-9.
Stadtfeld et al., "Induced pluripotent stem cells generated without viral integration." 2008, Science 322(5903):945-949.
Stafford and Prince, "Retinoic acid signaling is required for a critical early step in zebrafish pancreatic development." Curr. Biol. Jul. 23, 2002;12(14):1215-20.
Stahlman MT, et al., "Lamellar body formation in normal and surfactant protein B-deficient fetal mice." Lab. Invest. Mar. 2000;80(3):395-403.
Stott SRW, et al., "Foxa1 and Foxa2 Are Required for the Maintenance of Dopaminergic Properties in Ventral Midbrain Neurons at Late Embryonic Stages" Journal of Neuroscience. May 1, 2013;33(18):8022-34.
Suzuki R, et al., "Pvclust: an R package for assessing the uncertainty in hierarchical clustering." Bioinformatics. Jun. 15, 2006;22(12):1540-2.
Tadokoro, T, et al., BMP signaling and cellular dynamics during regeneration ofairway epithelium from basal progenitors. Development. Mar. 1, 2016;143(5):764-73.
Takebe T, et al., "Vascularized and functional human liver from an iPSC-derived organ bud transplant." Nature. Jul. 25, 2013;499(7459):481-4.
Thomson et al., "Embryonic stem cell lines derived from human blastocysts." 1998, Science 282 (5391):1145-1147.
Tiso, eta al., BMP signalling regulates anteroposterior endoderm patterning in zebrafish. Mech Dev. Oct. 2002;118(1-2):29-37.
Treutlein B, et al., "Reconstructing lineage hierarchies of the distal lung epithelium using single-cell RNA-seq." Nature. May 15, 2014;509(7500):371-5.
Van De Laar, et al., Cell surface marker profiling of human tracheal basal cells reveals distinct subpopulations, identifies MST1/MSP as a mitogenic signal, and identifies new biomarkers for lung squamous cell carcinomas. Respir Res. Dec. 31. 2014;15:160.
Vaughan, AE, et al. Lineage-negative progenitors mobilize to regenerate lung epithelium after major injury. Nature. Jan. 29, 2015;517(7536):621-5.
Vilain C, et al., "Autosomal dominant transmission of congenital thyroid hypoplasia due to loss-of-function mutation of PAX8." J. Clin. Endocrinol. Metab. Jan. 2001;86(1):234-8.
Volckaert T, et al., "Localized Fgf10 expression is not required for lung branching morphogenesis but prevents differentiation of epithelial progenitors" Development Sep. 2013; 140(18):3731-42.
Wan, et al., "Compensatory Roles of Foxa1 and Foxa2 during Lung Morphogenesis" J. Biol. Chem. 2005, 280,13809-13816.
Weaver M, et al., "Bmp4 and Fgf10 play opposing roles during lung bud morphogenesis." Development. 2000; 127(12):2695-704.
Weaver TE, et al., "Biogenesis of lamellar bodies, lysosome-related organelles involved in storage and secretion of pulmonary surfactant" Seminars in Cell & Developmental Biology. Aug. 2002;13(4):263-70.
Weeden, CE, et al. Lung Basal Stem Cells Rapidly Repair DNA Damage Using the Error-Prone Nonhomologous End-Joining Pathway. PLoS Biol. Jan. 26, 2017;15(1):e2000731.
Wells and Melton, "Early mouse endoderm is patterned by soluble factors from adjacent germ layers." Development, 2000, 127(8),1563-1572.
Wells JM, et al., "How to make an intestine." Development. Feb. 2014;141(4):752-60. PMCID: PMC3912826.
Wells, et al., "Vertebrate Endoderm Development" Annu. Rev. Cell Dev. Biol., 1999, 15,393-410.
Wickham H.; ggplot2: Elegant Graphics for Data Analysis—Hadley Wickham—Google Books. 2009, Table of Contents Only.
Woltjen et al., "piggyBac transposition reprograms fibroblasts to induced pluripotent stem cells" 2009, Nature 458:766-770.
Wong AP, et al., "Directed differentiation of human pluripotent stem cells into mature airway epithelia expressing functional CFTR protein" Nature Biotechnology, 2012, 30, 876-882.
Xue X, et al., "Endothelial PAS Domain Protein 1 Activates the Inflammatory Response in the Intestinal Epithelium to Promote Colitis in Mice" Gastroenterology. Jul. 13, 2013; 145(4): 831-841.
Yuan B, et al., "Inhibition of distal lung morphogenesis in Nkx2. 1(−/−) embryos." Dev. Dyn. Feb. 2000;217(2):180-90.
Zhang et al. "Expression of SHH signaling pathway components in the developing human lung." Histochem. Cell Biol. Oct. 2010;134(4):327-35.
Zhou et al., "Generation of induced pluripotent stem cells using recombinant proteins." 2009, Cell Stem Cell 4(5):381-384.
Zuo, W, et al. p63(+)Krt5(+) distal airway stem cells are essential for lung regeneration. Nature. Jan. 29, 2015;517(7536):616-20.

\* cited by examiner

FIG. 2G
FIG. 2H
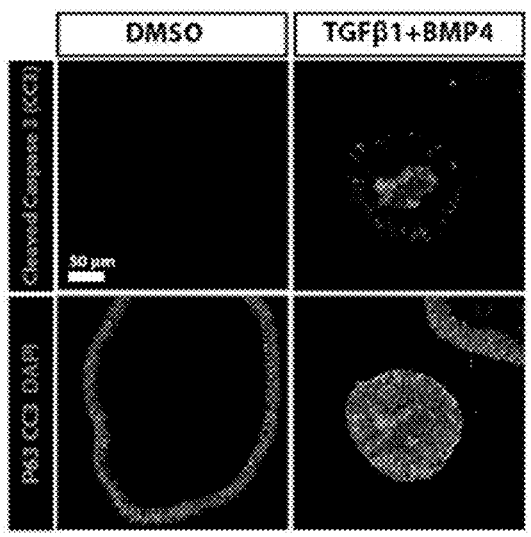
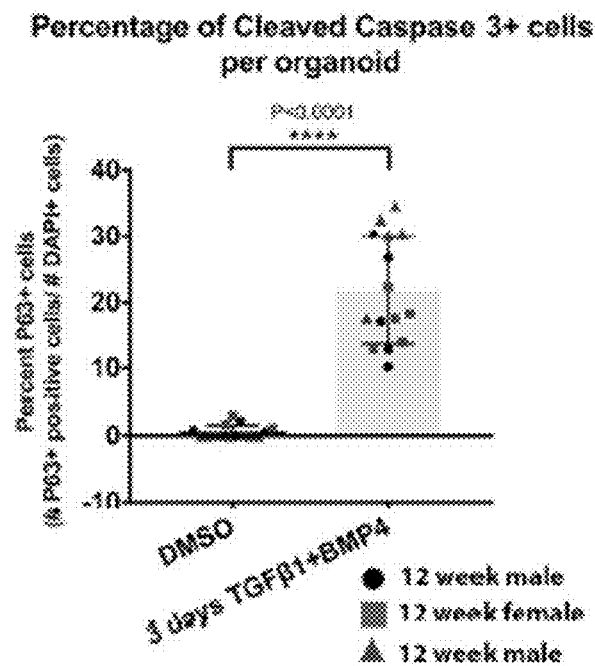
FIG. 2I
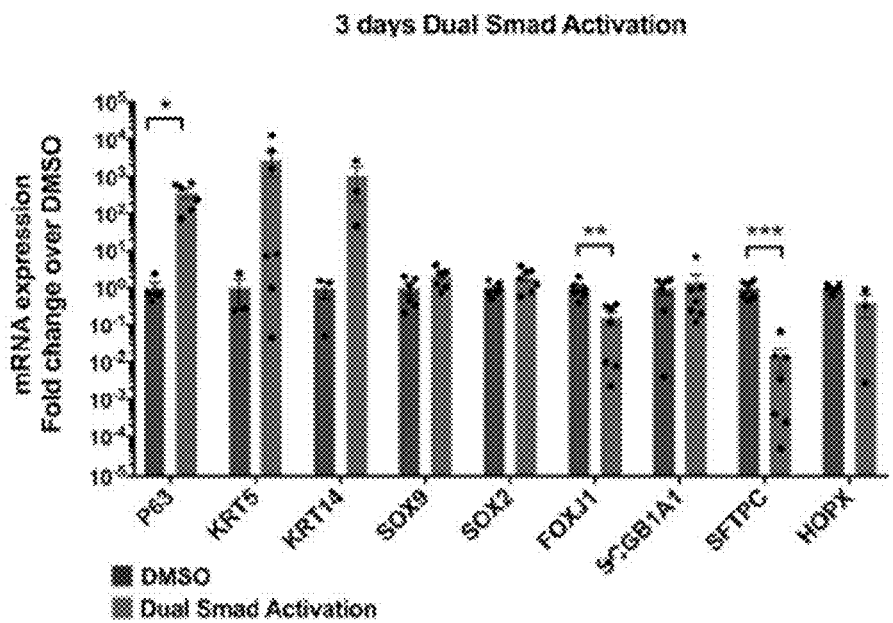

1. Bud Tip Maint. + DMSO (FGF7, CHIR99021, ATRA)
2. 3 days Dual Smad Activation (DSA; TGFβ1, BMP4, FGF7, CHIR99021, ATRA)
3. 3 days DSA – 1 week Bud Tip Maint. + DMSO (FGF7, CHIR99021, ATRA)
4. 3 days DSA – 1 week FGF10
5. 3 days DSA – 1 week FGF10 + Y27632
6. 3 days DSA – 1 week FGF10 + A8301 + NOG
7. 3 days DSA – 1 week FGF10 + A8301 + NOG + Y27632
8. 3 days DSA – 1 week FGF10 + A8301 + NOG + Y27632 + CHIR99021

FIG. 5E
FIG. 5F
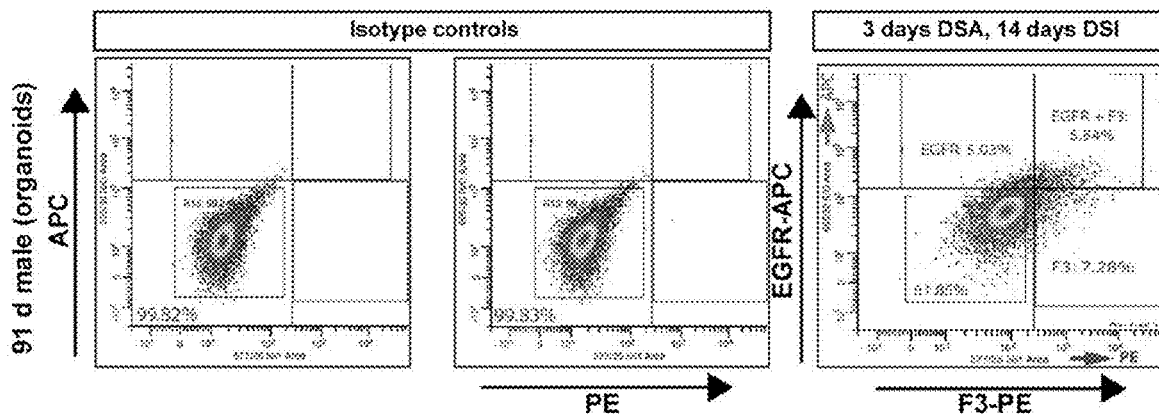
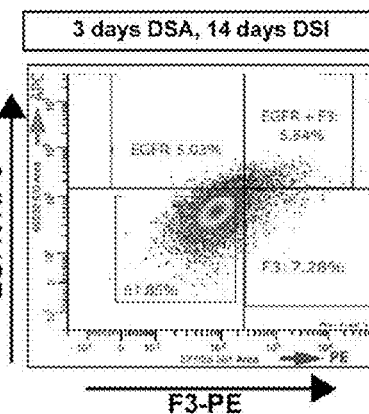
FIG. 5G
FIG. 5H
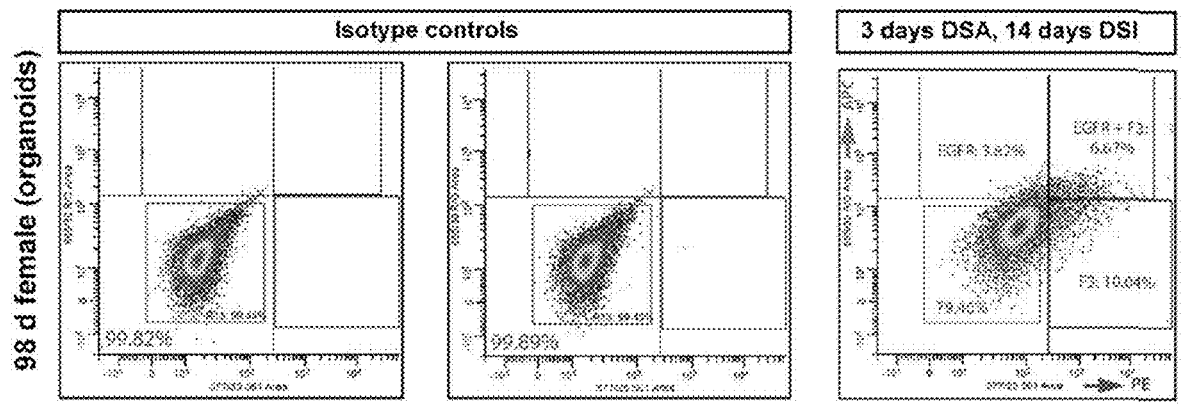
FIG. 5I
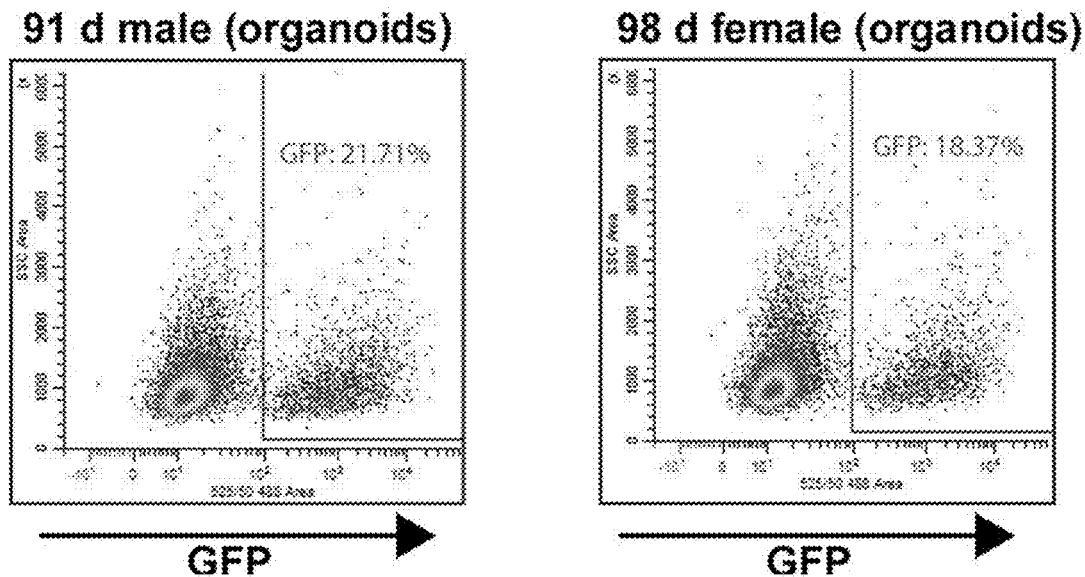

COMPOSITIONS AND METHODS FOR OBTAINING FUNCTIONAL BASAL-LIKE CELLS

CROSS-REFERENCE TO RELATED APPLICATIONS

The present invention claims the priority benefit of U.S. Provisional Patent Application 62/757,553, filed Nov. 8, 2018, which is hereby incorporated by reference.

FIELD OF THE INVENTION

The invention disclosed herein generally relates to methods and systems for converting stem cells into specific tissue(s) or cells through directed differentiation. In particular, the invention disclosed herein relates to methods and systems for promoting functional basal-like cells from pluripotent stem cell-derived lung bud tip progenitor organoid tissue through activation of SMAD signaling via activation of TGFβ1 (and/or the TGFβ signaling pathway) and BMP4 (and/or the BMP signaling pathway).

INTRODUCTION

Pluripotent stem cells (PSCs) are the descendants of totipotent cells and can differentiate into nearly all cells, i.e., cells derived from any of the three germ layers, including endoderm (interior stomach lining, gastrointestinal tract, the lungs), mesoderm (muscle, bone, blood, urogenital), and ectoderm (epidermal tissues and nervous system).

Embryonic and induced pluripotent stem cells have had an unprecedented impact on the ability to study human diseases and to generate replacement tissues that are therapeutically effective in animal models.

In developmental biology, cellular differentiation is the process by which a less specialized cell becomes a more specialized cell type. Most successful efforts to direct the differentiation of human PSCs into therapeutic cell types have been based on studies of embryonic organ development. Examples include the generation of liver hepatocytes and pancreatic endocrine cells, which have shown functional potential in animal models of liver disease and diabetes. Similarly, differentiation of PSCs into lung tissue may provide therapeutic benefit for diseases such as end stage lung disease.

Pluripotent stem cells have the potential to differentiate into any of the three germ layers: endoderm (interior stomach lining, gastrointestinal tract, the lungs), mesoderm (muscle, bone, blood, urogenital), and ectoderm (epidermal tissues and nervous system). As such, pluripotent stem cells can give rise to any fetal or adult cell type. However, the fate of the particular pluripotent stem cells is controlled by numerous cellular signaling pathway and numerous factors. Further, the pluripotent stem cells alone cannot develop into a fetal or adult animal because they lack the potential to contribute to extraembryonic tissue, such as the placenta.

What is needed in the art are methods and systems for accurately controlling the destination of the pluripotent stem cells in order to create the specific type of tissue or organism of desire.

The present invention addresses this need.

SUMMARY OF THE INVENTION

Experiments conducted during the course of developing embodiments for the present invention characterized the pluripotent stem cell-derived lung bud tip progenitor organoid tissue to basal stem cells using human fetal tissue specimens and bud tip progenitor organoid cultures. Analysis of human fetal lung specimens from 8-20 weeks gestation using single cell RNA sequencing (scRNAseq) identified molecular events, cell states, and inferred differentiation trajectories that revealed a previously un-described transitional cell state ('hub progenitors') during bud tip-to-airway differentiation. Further, this analysis implicated Small Mothers Against Decapentaplegic (SMAD) signaling as a regulator of the bud tip-to-basal cell transition. Indeed, such experiments demonstrated that functional in vitro studies utilizing bud tip progenitor organoids supported the observation that activation of SMAD signaling via TGFβ1 and BMP4 robustly induced the transition into functional basal-like cells, which exhibited clonal expansion, self-renewal and multilineage differentiation. Such experiments provide a framework for deducing and validating key regulators of cell fate decisions using single cell transcriptomics and human organoid models, and provides important context for beginning to understand normal and abnormal human lung development. Further, the identification of SMAD signaling as a critical regulator of newly born basal cells in the lung provides implications for regenerative medicine, basal cell development in other organs, and understanding basal cell misregulation in disease.

Accordingly, the invention disclosed herein generally relates to methods and systems for converting stem cells into specific tissue(s) or cells through directed differentiation. In particular, the invention disclosed herein relates to methods and systems for promoting functional basal-like cells from pluripotent stem cell-derived lung bud tip progenitor organoid tissue through activation of SMAD signaling via activation of TGFβ1 (and/or the TGFβ signaling pathway) and BMP4 (and/or the BMP signaling pathway).

In certain embodiments, the present invention provides methods of inducing formation of functional basal-like cells, comprising culturing stem cell-derived lung bud tip progenitor organoid tissue in vitro, wherein the culturing results in differentiation of the stem cell-derived lung bud tip progenitor organoid tissue into tissue comprising functional basal-like cells, wherein the culturing comprises activating the SMAD signaling pathway via activation of TGFβ1 (and/or the TGFβsignaling pathway) and BMP4 (and/or the BMP signaling pathway); and obtaining functional basal-like cells from the cultured stem cell-derived lung bud tip progenitor organoid tissue.

In some embodiments, the stem cell-derived lung bud tip progenitor organoid tissue is derived from pluripotent stem cells. In some embodiments, the pluripotent stem cells are embryonic stem cells and/or induced pluripotent stem cells. In some embodiments, the pluripotent stem cells are human pluripotent stem cells.

In some embodiments, the culturing and obtaining steps are conducted in vitro.

In some embodiments, the obtained functional basal-like cells have one or more of the following characteristics: increased TP63 expression, increased KRT5 expression, increased KRT14 expression, increased EGFR expression, and increased F3 expression. In some embodiments, the obtained basal stem cells are capable of clonal expansion. In some embodiments, the obtained basal stem cells are capable of self-renewal. In some embodiments, the obtained basal stem cells are capable of multilineage differentiation.

Such methods are not limited to a particular manner of activating BMP4 and/or the BMP signaling pathway within the stem cell-derived lung bud tip progenitor organoid tissue. In some embodiments, activating the BMP signaling pathway within the stem cell-derived lung bud tip progenitor organoid tissue is accomplished through culturing the stem cell-derived lung bud tip progenitor organoid tissue with a small molecule or agonist. In some embodiments, the small molecule or agonist that activates BMP signaling pathway is BMP4. In some embodiments, the small molecule or agonist that activates BMP signaling pathway is selected from BMP2, BMP3, BMP4, BMP5, BMP6, BMP7, BMP8a and 8b, BMP10, BMP11 and BMP15.

Such methods are not limited to a particular manner of activating the TGFβ signaling pathway within the stem cell-derived lung bud tip progenitor organoid tissue. In some embodiments, activating the TGFβ signaling pathway within the stem cell-derived lung bud tip progenitor organoid tissue is accomplished through culturing the stem cell-derived lung bud tip progenitor organoid tissue with a small molecule or agonist. In some embodiments, the small molecule or agonist that activates the TGFβ signaling pathway is TGFβ1. In some embodiments, the small molecule or agonist that activates the TGFβ signaling pathway is TGFβ1, TGFβ2, or TGFβ3.

In some embodiments, the methods further comprise culturing the obtained functional basal-like cells with FGF10 and Y27632. In some embodiments, the methods comprise culturing the stem cell-derived lung bud tip progenitor organoid tissue to obtain functional basal-like cells, and culturing the obtained functional basal-like cells with FGF10, Y27632, and one or more inhibitors of SMAD signaling (e.g., an inhibitor of the TGFβ signaling pathway and an inhibitor of the BMP signaling pathway). Such embodiments are not limited to a specific TGFβ signaling pathway inhibitor. In some embodiments, the TGFβ signaling pathway inhibitor is A8308. Such embodiments are not limited to a specific BMP signaling pathway inhibitor. In some embodiments, the BMP signaling pathway inhibitor is Noggin.

In some embodiments, culturing the obtained functional basal-like cells with FGF10, Y27632, and one or more inhibitors of SMAD signaling (e.g., an inhibitor of the TGF signaling pathway and an inhibitor of the BMP signaling pathway) (e.g., A8308 and Noggin) occurs over a specified temporal period.

In some embodiments, culturing the obtained functional basal-like cells with FGF10, Y27632, and one or more inhibitors of SMAD signaling (e.g., an inhibitor of TGFβ1 and/or the TGFβ signaling pathway and an inhibitor of BMP4 and/or the BMP signaling pathway) (e.g., A8308 and Noggin) occurs simultaneously or does not occur simultaneously.

In certain embodiments, the present invention provides compositions comprising or consisting of functional basal-like cells produced in vitro from the described methods.

In certain embodiments, the present invention provides kits comprising functional basal-like cells produced in vitro from the described methods.

In certain embodiments, the present invention provides methods for directing differentiation of pluripotent stem cell-derived lung bud tip progenitor organoid tissue to functional basal-like cells, comprising: (i) contacting the pluripotent stem cell-derived lung bud tip progenitor organoid tissue with a composition comprising a BMP4 pathway activator, and a TGFβ1 activator to obtain functional basal-like cells, wherein the functional basal-like cells are capable of one or more of clonal expansion, self-renewal, and multilineage differentiation. In some embodiments, the composition further comprises culturing the obtained functional basal-like cells with FGF10 and Y27632 and one or more inhibitors of the TGFβ and BMP signaling pathways (e.g., A8308 and Noggin).

Figure 1A:
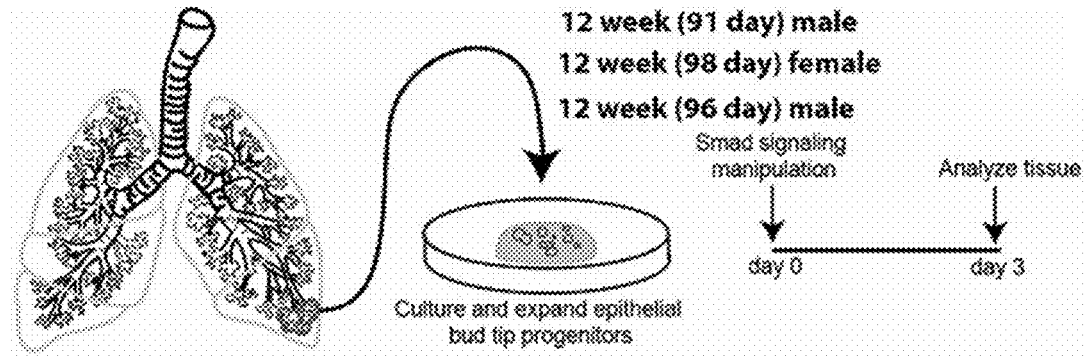
FIG. 1A-M: in vitro generation of functional basal stem cells from human fetal bud tip progenitors. a) Schematic of experimental design. Bud tip progenitors were enzymatically and mechanically isolated from n=3 12 week human fetal lungs as previously described (see, Miller A J, et al. (2018) Stem Cell Reports 10(1):101-119) and expanded as 3-dimensional organoids in Matrigel droplets in serum-free progenitor expansion medium (FGF7, CHIR99021, ATRA, see methods). Once cultures were established, they were treated with serum-free progenitor maintenance medium supplemented with combinations of activators and/or inhibitors of TGFβ and BMP. Organoids were collected after 3 days in culture and analyzed for mRNA and protein expression. b) At least 1 well, containing 20-50 organoids, for each biological replicate was collected and RNA was extracted for QRT-PCR analysis. For some groups, more than 1 well of organoids was collected per biological replicate and served as a technical replicate. Expression of TP63 was evaluated by QRT-PCR for all treatment groups. Treatment for 3 days with supplementation of both TGFβ1 (100 ng/mL) and BMP4 (100 ng/mL) led to a significant increase in TP63 expression relative to all other groups (One-way ANOVA, multiple comparisons of the mean of each group versus the mean in all other groups, p<0.0001; 3 days TGFβ1 and BMP4 referred to as dual SMAD activation or DSA). Data is plotted as arbitrary units. Error bars are plotted to show mean +/− the standard error of the mean. Data is from a single experiment and is representative of n=3 experiments. c) Protein staining of fetal bud tip progenitor organoids shows very-low to absent TP63+ staining (green) in DMSO treated controls, and a dramatic increase in the number of cells positive for TP63 after 3 days of treatment with TGFβ1 and BMP4. KRT5 (pink) was not detected in any cells in the control group nor after 3 days of TGFβ and BMP4 treatment. Scale bar represents 50 µm. d) Quantification of (c). Total number of TP63+ cells were counted for 3-9 individual organoids across 3 biological replicates. DMSO treated controls exhibited 0.125% (+/−0.08%) TP63+ cells, whereas 60.13% (+/−3.035%) of cells within organoids treated with 3 days of TGFβ1 and BMP4 showed positive TP63 staining. e) QRT-PCR of DMSO (gray bars) and TGFβ1/BMP4 (dual SMAD activation; blue bars) treated organoids after 3 days of treatment plotted as fold change over DMSO controls. DSA treated organoids exhibited a 370-fold increase over DMSO controls in TP63 expression. This increase was statistically significant (Mann-Whitney test, p=0.0238). While expression of another basal cell marker, KRT5, trended upwards after DSA treatment, there was large variability between samples and this increase was not statistically significant (Mann-Whitney test, p>0.05). This is consistent with protein staining data showing little to no detectable KRT5 protein after 3 days DSA, and is also consistent with 'early' basal cells in the lower airway being KRT5− at 12 weeks gestation. Error bars represent the mean +/− the standard error of the mean. e) Experimental schematic. Fetal bud tip progenitor organoids were treated with DSA for 3 days and then treated with various combinations of growth factors to identify conditions that maintained and expanded TP63+ population of cells. g) DSA treatment led to a severe reduction in proliferation and led to dense structures that did not expand.
Figure 1B:
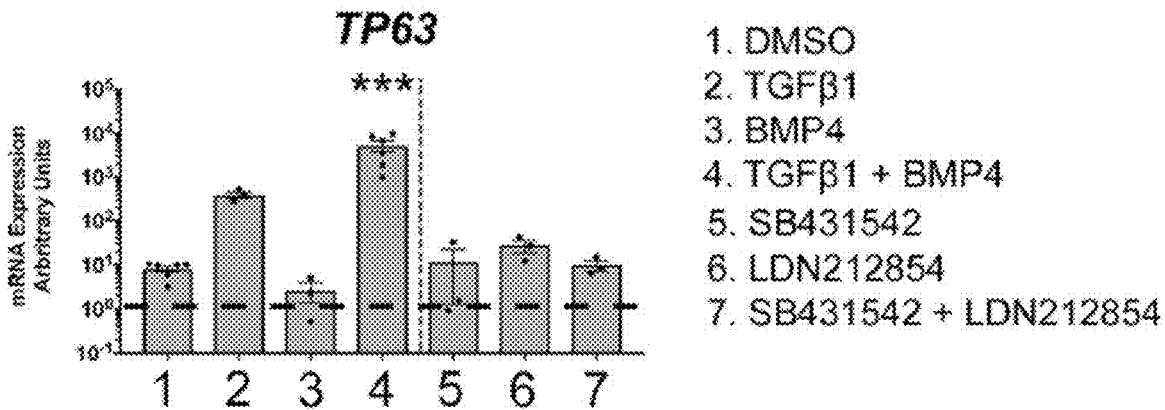

Treatment of organoids for 3 days of DSA followed by 7 days of culture conditions that included dual SMAD inhibition (A8308, NOGGIN) along with FGF10 and Y27632, a ROCK inhibitor, led to survival and expansion of organoids. Scale bar represents 500 μm. h) QRT-PCR of DMSO (gray bars) and DSA followed by 7 days basal cell expansion (blue bars) treated organoids after 10 total days of treatment plotted as fold change over DMSO controls. Treated organoids exhibited a 394-fold increase over DMSO controls in mean TP63 expression and a 13-fold increase in mean KRT5 expression. Neither increase was statistically significant (Mann-Whitney Test, p>0.5). Error bars represent the mean +/− the standard error of the mean. i) Organoids treated for 3 days with DSA followed by 7 days of basal cell expansion in supplemented dual smad inhibition medium contained TP63+ cells that also stained positive for cell surface basal cell markers EGFR and F3, as identified in FIG. 1 from human fetal scRNAseq. j) Experimental overview of cell sorting and clonal expansion experiment. 12 week fetal bud tip progenitor organoids (n=3 biological replicates) were broken into small clumps and infected with a lentiviral construct carrying GFP under a CMV promoter. GFP integrated randomly and resulting orgaoids contained mixed populations of GFP+ and GFP− cells. Organoids were then treated with 3 days DSA to induce TP63 expression, followed by 18-19 days of treatment with basal cell expansion medium. After 18 days of expansion, organoids were broken into single cells, stained with protein antibodies raised against EGFR and F3, and subjected to Fluoresence Activated Cell Sorting (FACS). k) Immediately after cell sorting, 20% of the sorted cells from each group were subjected to light (600 g) centrifugation on a cytospin for 5 minutes on to a glass slide, and slides were stained for TP63 to identify the percentage of cells in each sorted group that was TP63+. 92.09% of double positive (EGFR+/F3+) cells exhibited nuclear TP63 staining, compared to 36.39% and 42.17% of EGFR-only and F3-only positive groups, respectively, and only 8.09% of double negative (EGFR−/F3−) cells. Error bars represent the mean +/− the standard error of the mean. l) After sorting, all remaining cells from each group were plated in a Matrigel droplet and allowed to expand for 14-53 days in basal cell expansion medium, after which they were collected and processed for protein staining and single cell RNAseq (FIG. 4). Protein staining revealed the presence of SCGB1A1 (pink) club-like cells and AcTUB+ and FOXJ1+ multiciliated cells (white), first two panels from left. KRT8 (green) strongly stains the cells on the apical surface in some organoids that contain a pseudo-stratified epithelium, like in the second panel from left. Positive staining for TP63 was detected in cells on the basolateral surface of pseudostratified epithelia (pink, right panel), and MUC5AC+(pink) goblet-like cells were also observed. Scale bar represents 50 μm. m) GFP (green) and brightfield images of whole organoids 53 days after cell sorting. All organoids were either entirely GFP+ or entirely GFP−, suggesting clonal expansion from a single cell.

FIG. 2A-I: Screen for growth factor combinations that induce TP63 expression in fetal bud tip progenitor organoids. a) Schematic of experimental design. Bud tip progenitors were enzymatically and mechanically isolated from n=3 12 week human fetal lungs as previously described (see, Miller A J, et al. (2018) Stem Cell Reports 10(1):101-119) and expanded as 3-dimensional organoids in Matrigel droplets in serum-free progenitor expansion medium (FGF7, CHIR99021, ATRA, see methods). Once cultures established, they were treated with serum-free progenitor maintenance medium supplemented with combinations of activators and/or inhibitors of TGFβ and BMP signaling. Organoids were collected after 3 days in culture and analyzed for mRNA and protein expression. b) At least 1 well, containing 20-50 organoids, for each biological replicate was collected and RNA was extracted for QRT-PCR analysis. For some groups, an additional well of organoids was collected per biological replicate and served as a technical replicate. QRT-PCR for KRT5 showed no significant changes in expression for any group (one-way ANOVA, p>0.05). Data is presented as mean +/− the standard error of the mean. c) Brightfield images of a single well of organoids for each group at day 0 and after 3 days of treatment. Treatment with TGFβ1 alone or TGFβ and BMP4 led to a reduction in organoid growth, an increase in apparent density of the organoids, and the appearance of many dead cells and debris around the organoids. d) Experiments were conducted that tested whether the presence of CHIR99021, a ROCK inhibitor and potent activator of the WNT pathway, affected the outcome of SMAD manipulation on TP63 expression. 1 well, containing 20-50 organoids, for each biological replicate was collected and RNA was extracted for QRT-PCR analysis. No statistical differences were observed between groups treated in the presence or absence of CHIR99021, though it was noted that variability within groups is high (one-way ANOVA, p>0.05). For this work, experiments were conducted that continued to include CHIR99021 in the dual smad activation (DSA) medium because it seemed to improve survival of organoid cultures. Data is reported as arbitrary units and error bars represent the mean +/− the standard error of the mean. e) Protein staining of proliferation marker KI67 (pink) and TP63 (green) in organoids treated with DMSO or with 3 days of DSA shows that DMSO treated organoids are very proliferative and do not contain any TP63+ cells, whereas organoids treated with 3 days of DSA medium exhibit very few proliferating cells and many TP63+ cells. DSA treated organoids also exhibit a denser morphology. Scale bars represent 50 μm. f) Quantification of e. Total number of KI67+ cells were counted for 4-5 individual organoids across 3 biological replicates. DMSO treated controls exhibited 31.04% (+/−9.79%) KI67+ cells, whereas 0.54% (+/−2.53%) of cells within organoids treated with 3 days of DSA showed positive KI67 staining. DSA treated organoids exhibited a statistically significant decrease in the number of KI67+ cells (Mann-Whitney test, P<0.0001). g) Protein staining of apoptosis marker Cleaved Caspase 3 (CC3; pink) and TP63 (green) in organoids treated with DMSO or with 3 days of DSA shows that DMSO treated organoids do not exhibit any apoptosis staining and do not contain any TP63+ cells, whereas organoids treated with 3 days of DSA medium exhibit a dramatic increase in CC3+ cells and many TP63+ cells. DSA treated organoids also exhibit a denser morphology. Scale bar represent 50 μm. f) Quantification of g. Total number of CC3+ cells were counted for 5 individual organoids across 3 biological replicates. DMSO treated controls exhibited 0.64% (+/−0.25%) CC3+ cells, whereas 21.86% (+/−2.12%) of cells within organoids treated with 3 days of DSA showed positive CC3 staining. DSA treated organoids exhibited a statistically significant increase in the number of CC3+ cells -Mann-Whitney test, p<0.0001). i) QRT-PCR for markers of canonical differentiated lung epithelial cell types showing DMSO (gray bars) and DSA treated (blue bars) organoids after 3 total days of treatment. Data is plotted as fold change over DMSO controls. DSA treated organoids exhibited a 370-fold increase over DMSO controls in mean TP63 expression, a 2780-fold increase in mean KRT5 expression and a 1045-fold increase in mean KRT14 expression, all basal cell markers. TP63 expression was statistically significantly higher than DMSO controls (Mann-Whitney Test, p=0.0238), but the increases in KRT5 and KRT14 were not statistically significant. No other markers exhibited increases in expression after 3 days of DSA treatment. Some markers exhibited a significant reduction in expression, including the ciliated cell marker FOXJ1 (Mann-Whitney Test, p=0.02) and bud tip progenitor marker/AECII marker SFTPC (Mann-Whitney Test, p=0.002). Error bars represent the mean +/− the standard error of the mean.

FIG. 3A-E: Screen for factors that maintain growth and expansion of TP63+ cells in culture. a) Experimental schematic. Fetal bud tip progenitor organoids were treated with DSA for 3 days and then treated with various combinations of growth factors for an additional 7 days to identify conditions that maintained and expanded TP63+ population of cells (10 days total). Experimental conditions are listed as groups 1-8. b) Brightfield images of organoids 10 days after treatment. Treatment with group 7 medium led to the best expansion and survival of organoids. Scale bar represents 500 μm. c) After 7 days of expansion in group 7 medium (Dual Smad Inhibition; DSI), organoids maintained cells that expressed TP63 (green), and some cells even exhibited staining for mature basal cell marker KRT5 (pink). ECAD marks the cell membrane (white). No cells expressed other basal cell marker PDPN (pink), nor did any cells express the bud tip adjacent/AECI marker RAGE (white). Scale bar represents 50 μm. c) 1 well, containing 20-50 organoids, for each biological replicate was collected and RNA was extracted for QRT-PCR analysis. Expression of TP63 was evaluated by QRT-PCR for all treatment groups. Treatment for 3 with DSA led to a statistically significant increase in TP63 expression over DMSO controls. Treatment with DSA followed by 7 days of treatment with medium in group 7 (FGF10, A8301, NOGGIN, Y2763) or group 8 (FGF10, A8301, NOGGIN, Y2763, CHIR99021) medium led to a significant increase in TP63 expression compared with the DMSO control (One-way ANOVA, multiple comparisons of the mean of each group versus the mean in all other groups, p values are reported on the graph. p<0.05=*; p<0.01=, p<0.001=*, p<0.0001=****). Data is plotted as arbitrary units. Error bars are plotted to show mean +/− the standard error of the mean. Data is from a single experiment and is representative of n=3 experiments. e) QRT-PCR for markers of canonical differentiated lung epithelial cell types showing DMSO (gray bars) and DSA-DSI treated (blue bars) organoids after 3 days DSI and 7 days DSI treatment. Data is plotted as fold change over DMSO controls. DSA-DSI treated organoids exhibited a 394-fold increase over DMSO controls in meanTP63 expression. No markers exhibited statistically significant increases or decreases in expression after treatment, although trends suggest an increase in TP63, ciliated cell marker FOXJ1 and club cell marker SCGB1A1. Error bars represent the mean +/− the standard error of the mean.

FIG. 4A-E: Sorting and clonal expansion of fetal bud tip progenitor organoids. a) Bud tip progenitor organoids from n=3 biological replicates from 12 week fetal lungs were maintained in serum-free progenitor maintenance medium (FGF7, CHIR99021, ATRA) for 56 days. Staining for markers of differentiated lung epithelial cell types determined that bud tip progenitor organoids did not contain any differentiated cell types (club cell marker SCGB1A1 (pink), neuroendocrine markers Chromagranin A (CHGA; pink) and synaptophysin (SYN; white), ciliated cell marker FOXJ1 (white), basal cell marker TP63 (pink), goblet cell marker mucin 5AC (MUC5AC; white), AECII marker ABCA3 (pink), AECI and hub progenitor cell marker HOPX (green), secretory lineage marker PLUNC (white)). The majority of bud tip progenitor organoid cells were SOX9+(white). Scale bar represents 100 μm. b) 12 week fetal bud tip progenitor organoids (n=3 biological replicates) were broken into small clumps and infected with a lentiviral construct carrying GFP under a CMV promoter. GFP integrated randomly and resulting organoids contained mixed populations of GFP+ and GFP− cells. Organoids were then treated with 3 days DSA to induce TP63 expression, followed by 18-19 days of treatment with basal cell expansion medium. After 18 days of expansion, organoids were broken into single cells, stained with protein antibodies raised against EGFR and F3, and subjected to Fluoresence Activated Cell Sorting (FACS). After 53 days of expansion in serum-free basal cell expansion dual SMAD inhibition medium (FGF10, A8301, NOGGIN, Y27632) organoids were collected and fixed for protein staining. Staining for AECI and hub progenitor marker HOPX (green) was negative, as was staining for AECII marker ABCA3 (pink). Organoids grew clonally, with organoids being either entirely GFP negative or GFP positive (GFP, green, second panel). Many cells exhibited positive staining for club cell marker SCGB1A1 (pink), but staining for secretory lineage marker PLUNC (white) was undetected. In EGFR+/F3+ clonal organoids, no neuroendocrine cells were detected (CHGA, pink; SYN, white), though these cells were clearly detected in unsorted organoids. Scale bar represents c) Organoids that had been infected with GFP lentivirus but not sorted and left to expand in basal cell expansion medium were collected after 56 days in culture and stained for differentiated epithelial cell markers. Unsorted organoids exhibited clear positive staining for club cell marker SCGB1A1 (pink) and multiciliated markers Acetylated Tubulin (white) and FOXJ1 (white). Neuroendocrine cells were clearly detected (CHGA, pink; SYN, white). Organoids also exhibited TP63+ cells (pink) and cells that stained positive for goblet cell marker MUC5AC (white). Scale bar represents 50 μm. d) Unsorted organoids also did not show any positive staining for AECI/hub progenitor marker HOPX (green), or AECII marker ABCA3 (pink). Consistent with results from sorted organoids, the secretory lineage marker PLUNC was not detected (white). Scale bar represents 50 μm. e) Graph of the percent of GFP+ organoids versus total number of organoids from each group. The total number of organoids counted per group is reported. 2 wells of multiple organoids were counted for each biological replicate for the EGFR+/F3+ group.

FIG. 5A-I: Fluorescence Activated Cell Sorting of fetal bud tip progenitor organoid-derived basal-like cells. a) Feature plots of all tracheal epithelial cells combined for 15, 18 and 21 week fetal lung scRNAseq from FIG. 1 showing that the majority of TP63+ cells that express basal cell markers KRT5 and KRT15 and EGFR and F3 (green dots) also express TP63, EGFR and F3 (b) red dots). c) Fluorescence Activated Cell Sorting (FACS) plots for biological replicate 1. Isotype controls for APC and PE show 99.30% of cells were negative for both markers. d) Sorting on EGFR-APC and F3-PE sorted 25.90% of all cells to the double positive group. e) Fluorescence Activated Cell Sorting (FACS) plots for biological replicate 2. Isotype controls for APC and PE show 99.82% of cells were negative for APC and 99.83% were negative for PE. f) Sorting on EGFR-APC and F3-PE sorted 5.84% of all cells to the double positive group. g) Fluorescence Activated Cell Sorting (FACS) plots for biological replicate 3. Isotype controls for APC and PE show 99.82% of cells were negative APC and 99.89 cells were negative for F3. h) Sorting on EGFR-APC and F3-PE sorted 6.67% of all cells to the double positive group. i) Flow sorting identified 21.71% of cells from biological replicate 2 were GFP+ and 18.37% of cells from biological replicate 3 were GFP+.

FIG. 6A-D: Basal cell induction from hPSC-derived bud tip progenitor organoids. a) Schematic of experimental design. hPSC-derived bud tip progenitor organoids were generated as previously described.[1] Organoids were treated for 3 days with DSA to induce TP63, then cultured for an additional 42 days with basal cell expansion medium. b) 3 days after DSA treatment, many more TP63+ cells were observed in the DSA treated group compared to organoids on day 0 prior to DSA treatment. c) QRT-PCR analysis of each group for TP63 revealed a significant increase in expression for bud tip progenitor organoids after 3 days of DSA treatment (one-way ANOVA, $p<0.01$ , $p<0.001$ *). d) After 45 days in culture, bud tip organoids exhibited TP63+ cells, a pseudostratified epithelium as evidenced by KRT8 (green) staining on the luminal cells only, and the presence of multiciliated (AcTUB, white) and mucous producing cells (SCGB1A1, pink). Scale bar represents 50 µm.

DEFINITIONS

As used herein, the term "pluripotent stem cells (PSCs)," also commonly known as PS cells, encompasses any cells that can differentiate into nearly all cells, i.e., cells derived from any of the three germ layers (germinal epithelium), including endoderm (interior stomach lining, gastrointestinal tract, the lungs), mesoderm (muscle, bone, blood, urogenital), and ectoderm (epidermal tissues and nervous system). PSCs can be the descendants of totipotent cells, derived from embryonic stem cells (including embryonic germ cells) or obtained through induction of a non-pluripotent cell, such as an adult somatic cell, by forcing the expression of certain genes.

As used herein, the term "embryonic stem cells (ESCs)," also commonly abbreviated as ES cells, refers to cells that are pluripotent and derived from the inner cell mass of the blastocyst, an early-stage embryo. For purpose of the present invention, the term "ESCs" is used broadly sometimes to encompass the embryonic germ cells as well.

As used herein, the term "induced pluripotent stem cells (iPSCs)," also commonly abbreviated as iPS cells, refers to a type of pluripotent stem cells artificially derived from a normally non-pluripotent cell, such as an adult somatic cell, by inducing a "forced" expression of certain genes.

As used herein, the term "precursor cell" encompasses any cells that can be used in methods described herein, through which one or more precursor cells acquire the ability to renew itself or differentiate into one or more specialized cell types. In some embodiments, a precursor cell is pluripotent or has the capacity to becoming pluripotent. In some embodiments, the precursor cells are subjected to the treatment of external factors (e.g., growth factors) to acquire pluripotency. In some embodiments, a precursor cell can be a totipotent (or omnipotent) stem cell; a pluripotent stem cell (induced or non-induced); a multipotent stem cell; an oligopotent stem cells and a unipotent stem cell. In some embodiments, a precursor cell can be from an embryo, an infant, a child, or an adult. In some embodiments, a precursor cell can be a somatic cell subject to treatment such that pluripotency is conferred via genetic manipulation or protein/peptide treatment.

In developmental biology, cellular differentiation is the process by which a less specialized cell becomes a more specialized cell type. As used herein, the term "directed differentiation" describes a process through which a less specialized cell becomes a particular specialized target cell type. The particularity of the specialized target cell type can be determined by any applicable methods that can be used to define or alter the destiny of the initial cell. Exemplary methods include but are not limited to genetic manipulation, chemical treatment, protein treatment, and nucleic acid treatment.

As used herein, the term "cellular constituents" are individual genes, proteins, mRNA expressing genes, and/or any other variable cellular component or protein activities such as the degree of protein modification (e.g., phosphorylation), for example, that is typically measured in biological experiments (e.g., by microarray or immunohistochemistry) by those skilled in the art. Significant discoveries relating to the complex networks of biochemical processes underlying living systems, common human diseases, and gene discovery and structure determination can now be attributed to the application of cellular constituent abundance data as part of the research process. Cellular constituent abundance data can help to identify biomarkers, discriminate disease subtypes and identify mechanisms of toxicity.

As used herein, the term "organoid" is used to mean a 3-dimensional growth of mammalian cells in culture that retains characteristics of the tissue in vivo, e.g. prolonged tissue expansion with proliferation, multilineage differentiation, recapitulation of cellular and tissue ultrastructure, etc.

DETAILED DESCRIPTION OF THE INVENTION

The lungs of mammals including those of humans, have a soft, spongelike texture and are honeycombed with epithelium, having a much larger surface area in total than the outer surface area of the lung itself.

Breathing is largely driven by the muscular diaphragm at the bottom of the thorax. Contraction of the diaphragm pulls the bottom of the cavity in which the lung is enclosed downward, increasing volume and thus decreasing pressure, causing air to flow into the airways. Air enters through the oral and nasal cavities; it flows through the pharynx, then the larynx and into the trachea, which branches out into the main bronchi and then subsequent divisions. During normal breathing, expiration is passive and no muscles are contracted (the diaphragm relaxes). The rib cage itself is also able to expand and contract to some degree through the use of the intercostal muscles, together with the action of other respiratory and accessory respiratory muscles. As a result, air is transported into or expelled out of the lungs.

In humans, the trachea divides into two main bronchi that enter the roots of the lungs. The bronchi continue to divide within the lung, and after multiple divisions, give rise to bronchioles. The bronchial tree continues branching until it reaches the level of terminal bronchioles, which lead to alveolar sacs. Alveolar sacs, are made up of clusters of alveoli, like individual grapes within a bunch. The individual alveoli are tightly wrapped in blood vessels and it is here that gas exchange actually occurs. Deoxygenated blood from the heart is pumped through the pulmonary artery to the lungs, where oxygen diffuses into blood and is exchanged for carbon dioxide in the haemoglobin of the erythrocytes. The oxygen-rich blood returns to the heart via the pulmonary veins to be pumped back into systemic circulation.

Human lungs are located in two cavities on either side of the heart. Though similar in appearance, the two are not identical. Both are separated into lobes by fissures, with three lobes on the right and two on the left. The lobes are further divided into segments and then into lobules, hexagonal divisions of the lungs that are the smallest subdivision visible to the naked eye. The connective tissue that divides lobules is often blackened in smokers. The medial border of the right lung is nearly vertical, while the left lung contains a cardiac notch. The cardiac notch is a concave impression molded to accommodate the shape of the heart.

Each lobe is surrounded by a pleural cavity, which consists of two pleurae. The parietal pleura lies against the rib cage, and the visceral pleura lies on the surface of the lungs. In between the pleura is pleural fluid. The pleural cavity helps to lubricate the lungs, as well as providing surface tension to keep the lung surface in contact with the rib cage.

Lungs are to a certain extent "overbuilt" and have a tremendous reserve volume as compared to the oxygen exchange requirements when at rest. Such excess capacity is one of the reasons that individuals can smoke for years without having a noticeable decrease in lung function while still or moving slowly; in situations like these only a small portion of the lungs are actually perfused with blood for gas exchange. Destruction of too many alveoli over time leads to the condition emphysema, which is associated with extreme shortness of breath. As oxygen requirements increase due to exercise, a greater volume of the lungs is perfused, allowing the body to match its $CO_2/O_2$ exchange requirements. Additionally, due to the excess capacity, it is possible for humans to live with only one lung, with the one compensating for the other's loss.

The environment of the lung is very moist, which makes it hospitable for bacteria. Many respiratory illnesses are the result of bacterial or viral infection of the lungs. Inflammation of the lungs is known as pneumonia; inflammation of the pleura surrounding the lungs is known as pleurisy.

Vital capacity is the maximum volume of air that a person can exhale after maximum inhalation; it can be measured with a spirometer. In combination with other physiological measurements, the vital capacity can help make a diagnosis of underlying lung disease.

The lung parenchyma is strictly used to refer solely to alveolar tissue with respiratory bronchioles, alveolar ducts and terminal bronchioles. However, it often includes any form of lung tissue, also including bronchioles, bronchi, blood vessels and lung interstitium.

Following gastrulation (embryonic day E7.5 in mice), the definitive endoderm undergoes complex morphogenetic movements that ultimately lead to the formation of the primitive gut tube. The foregut represents the most anterior (cranial) region of this tube, while the midgut and hindgut are located at progressively more posterior regions, towards the caudal end of the embryo (see, e.g., Wells, et al., Annu. Rev. Cell Dev. Biol. 15, 393-410). Transcription factor genes such as Foxa1, Foxa2, Gata4 and Gata6, which are expressed early in the endoderm, are crucial for the survival, differentiation and morphogenesis of the foregut (see, e.g., Kuo, et al., Genes Dev. 11, 1048-1060; Morrisey, et al., Genes Dev. 12, 3579-3590; Ang, et al., Cell 78, 561-574; Wan, et al., J. Biol. Chem. 280, 13809-13816). By E8.0-9.5, the local expression of transcription factors along the antero-posterior (AP) axis of the gut endoderm marks organ-specific domains (or fields). For example, the homeodomain protein gene Nkx2.1 [also known as thyroid transcription factor 1 (Titf1) or T/EBP] is expressed in the thyroid and respiratory fields (see, e.g., Kimura, et al., Genes Dev. 10, 60-69), Hex (hematopoietically expressed homeobox) is expressed in the thyroid and liver fields (see, e.g., Martinez Barbera, et al., Development 127, 2433-2445), and the Pdx1 (pancreas-duodenal-associated homeobox gene) is expressed in the pancreatic and duodenal fields (see, e.g., Offield, et al., Development 122, 983-995). In addition, morphogenetic movements foster dynamic interactions between the endoderm and neighboring structures, such as the heart, notochord or the septum transversum (the mesodermal cells that give rise to the diaphragm). Exposure of the endoderm to diffusible signals from these structures at crucial developmental windows is essential for endodermal cell fate specification (see, e.g., Kumar and Melton, Curr. Opin. Genet. Dev. 13, 401-407; Bort, et al., Development 131, 797-80).

Fibroblast growth factor 4 (Fgf4), bone morphogenetic protein 2 (Bmp2) and retinoic acid (RA) are among the signals that confer AP identity to the early endoderm. They render the endoderm competent to respond to signals from the adjacent mesoderm or from nearby structures to initiate morphogenesis (see, e.g., Tiso, eta al., Mech. Dev. 118, 29-37; Stafford and Prince, Curr. Biol. 12, 1215-1220; Wells and Melton, Development 127, 1563-1572). In zebrafish, disrupted RA signaling during gastrulation results in the loss of liver and pancreatic (posterior) fates, while thyroid and pharynx (anterior) fates remain unaltered. Conversely, excess RA induces hepatic and pancreatic cell fates at more anterior domains (see, e.g., Stafford and Prince; Curr. Biol. 12, 1215-1220). In mice and rats, RA signaling initiates soon after gastrulation (see, e.g., Rossant, et al., Genes Dev. 5, 1333-1344), but does not seem to be as crucial for foregut AP identity as it is in the zebrafish.

Basal stem cells (basal cells), located in the bronchi and trachea of the human lung epithelium, play a critical role in normal airway homeostasis and repair, and have been implicated in the development of diseases such as cancer (see, Rock J R, et al. (2009) Proceedings of the National Academy of Sciences 106(31):12771-12775; Hong K U, et al., (2004) AJPA 164(2):577-588; Weeden C E, et al. (2017) PLoS Biol 15(1):e2000731; Emily Van de Laar, et al., (2014) Respir Res 15(1). doi:10.1186/s12931-014-0160-8). Additionally, basal-like cells contribute to alveolar regeneration and fibrosis following severe injury (see, Vaughan A E, et al. (2015) Nature 517(7536):621-625; Zuo W, et al. (2015) Nature 517(7536):616-620). However, the developmental origin of basal cells is unclear. Previous work has shown that specialized progenitor cells exist at the tips of epithelial tubes during lung branching morphogenesis, and in mice, give rise to all alveolar and airway lineages (see, Rawlins E L, et al., (2009) Development 136(22):3741-3745). These 'bud tip progenitor cells' have also been described in the human fetal lung (see, Miller A J, et al. (2018) Stem Cell Reports 10(1):101-119; Nikolié M Z, et al. (2017) Elife 6. doi: 10.7554/eLife.26575; Danopoulos S, et al. (2018) AJP: Lung Cellular and Molecular Physiology 314(1):L144-L149), but the mechanisms controlling bud tip differentiation into specific cell lineages, including basal cells, are unknown.

Experiments conducted during the course of developing embodiments for the present invention characterized the "bud tip-to-basal cell transition" using human fetal tissue specimens and bud tip progenitor organoid cultures. Analysis of human fetal lung specimens from 8-20 weeks gestation using single cell RNA sequencing (scRNAseq) identified molecular events, cell states, and inferred differentiation trajectories that revealed a previously un-described transitional cell state ('hub progenitors') during bud tip-to-airway differentiation. Further, this analysis implicated SMAD signaling as a regulator of the bud tip-to-basal cell transition. Indeed, such experiments demonstrated that functional in vitro studies utilizing bud tip progenitor organoids supported the observation that activation of SMAD signaling via TGFβ1 and BMP4 robustly induced the transition into functional basal-like cells, which exhibited clonal expansion, self-renewal and multilineage differentiation. Such experiments provide a framework for deducing and validating key regulators of cell fate decisions using single cell transcriptomics and human organoid models, and provides important context for beginning to understand normal and abnormal human lung development. Further, the identification of SMAD signaling as a critical regulator of newly born basal cells in the lung provides implications for regenerative medicine, basal cell development in other organs, and understanding basal cell misregulation in disease.

Taken together, such experiments demonstrate an efficient and robust in vitro system to generate complex, functional basal-like cell formation.

Accordingly, the invention disclosed herein generally relates to methods and systems for converting stem cells into specific tissue(s) or cells through directed differentiation. In particular, the invention disclosed herein relates to methods and systems promoting functional basal-like cells from pluripotent stem cell-derived lung bud tip progenitor organoid tissue through activation of SMAD signaling via activation of TGFβ1 and BMP4.

In some embodiments, an important step is to obtain lung bud tip progenitor organoid tissue derived from stem cells that are pluripotent or can be induced to become pluripotent. In some embodiments, pluripotent stem cells are derived from embryonic stem cells, which are in turn derived from totipotent cells of the early mammalian embryo and are capable of unlimited, undifferentiated proliferation in vitro. Embryonic stem cells are pluripotent stem cells derived from the inner cell mass of the blastocyst, an early-stage embryo. Methods for deriving embryonic stem cells from blastocytes are well known in the art. For example, three cell lines (H1, H13, and H14) have a normal XY karyotype, and two cell lines (H7 and H9) have a normal XX karyotype. Additional stem cells that can be used in embodiments in accordance with the present invention include but are not limited to those provided by or described in the database hosted by the National Stem Cell Bank (NSCB), Human Embryonic Stem Cell Research Center at the University of California, San Francisco (UCSF); WISC cell Bank at the Wi Cell Research Institute; the University of Wisconsin Stem Cell and Regenerative Medicine Center (UW-SCRMC); Novocell, Inc. (San Diego, Calif.); Cellartis AB (Goteborg, Sweden); ES Cell International Pte Ltd (Singapore); Technion at the Israel Institute of Technology (Haifa, Israel); and the Stem Cell Database hosted by Princeton University and the University of Pennsylvania. Indeed, embryonic stem cells that can be used in embodiments in accordance with the present invention include but are not limited to SA01 (SA001); SA02 (SA002); ES01 (HES-1); ES02 (HES-2); ES03 (HES-3); ES04 (HES-4); ES05 (HES-5); ES06 (HES-6); BG01 (BGN-01); BG02 (BGN-02); BG03 (BGN-03); TE03 (13); TE04 (14); TE06 (16); UC01 (HSF1); UC06 (HSF6); WA01 (H1); WA07 (H7); WA09 (H9); WA13 (H13); WA14 (H14). In some embodiments, the stem cells are further modified to incorporate additional properties. Exemplary modified cell lines include but not limited to H1 Oct.4-EGFP; H9 Cre-LoxP; H9 hNanog-pGZ; H9 hOct4-pGZ; H9 in GFPhES; and H9 Syn-GFP. More details on embryonic stem cells can be found in, for example, Thomson et al., 1998, Science 282 (5391):1145-1147; Andrews et al., 2005, Biochem Soc Trans 33:1526-1530; Martin 1980, Science 209 (4458):768-776; Evans and Kaufman, 1981, Nature 292(5819): 154-156; Klimanskaya et al., 2005, Lancet 365 (9471): 1636-1641).

The present invention provides methods for directing the differentiation of pluripotent stem cell-derived lung bud tip progenitor organoid tissue into functional basal-like cells in vitro.

As such, in some embodiments, methods are provided for the directed differentiation of pluripotent stem cell-derived lung bud tip progenitor organoid tissue into functional basal-like cells, and obtaining of such functional basal-like cells.

Such methods are not limited to a particular manner of accomplishing the directed differentiation of pluripotent stem cell-derived lung bud tip progenitor organoid tissue into functional basal-like cells. Indeed, any method for producing functional basal-like cells from pluripotent stem cell-derived lung bud tip progenitor organoid tissue is applicable to the methods described herein.

In some embodiments, the pluripotent stem cell-derived lung bud tip progenitor organoid tissue is human pluripotent stem cell-derived lung bud tip progenitor organoid tissue. In some embodiments, the stem cell-derived lung bud tip progenitor organoid tissue is murine pluripotent stem cell-derived lung bud tip progenitor organoid tissue.

In some embodiments, the differentiation process from stem cell-derived lung bud tip progenitor organoid tissue into functional basal-like cells is accomplished through activation of SMAD signaling. Such methods are not limited to a particular manner of activating SMAD signaling. In some embodiments, activation of SMAD signaling is accomplished through activation of TGFβ1 (and/or the TGFβ signaling pathway) and BMP4 (and/or the BMP signaling pathway).

Such methods are not limited to a particular manner of activating BMP4 and/or the BMP signaling pathway within the stem cell-derived lung bud tip progenitor organoid tissue. In some embodiments, activating BMP4 and/or the BMP signaling pathway within the stem cell-derived lung bud tip progenitor organoid tissue is accomplished through culturing the stem cell-derived lung bud tip progenitor organoid tissue with a small molecule or agonist. In some embodiments, the small molecule or agonist that activates the BMP signaling pathway is BMP4. In some embodiments, the small molecule or agonist that activates BMP signaling pathway is selected from BMP2, BMP3, BMP4, BMP5, BMP6, BMP7, BMP8a and 8b, BMP10, BMP11 and BMP15.

Such methods are not limited to a particular manner of activating the TGFβ signaling pathway within the stem cell-derived lung bud tip progenitor organoid tissue. TGF-β signaling pathway is used to describe the downstream signaling events attributed to TGF-β and TGF-β like ligands. For example, in one signaling pathway a TGF-β ligand binds to and activates a Type II TGF-β receptor. The Type II TGF-β receptor recruits and forms a heterodimer with a Type I TGF-β receptor. The resulting heterodimer permits phosphorylation of the Type I receptor, which in turn phosphorylates and activates a member of the SMAD family of proteins. A signaling cascade is triggered, which is well known to those of skill in the art, and ultimately leads to control of the expression of mediators involved in cell growth, cell differentiation, tumorigenesis, apoptosis, and cellular homeostasis, among others. Other TGF-β signaling pathways are also contemplated for manipulation according to the methods described herein.

In some embodiments, activating the TGFβ signaling pathway within the stem cell-derived lung bud tip progenitor organoid tissue is accomplished through culturing the stem cell-derived lung bud tip progenitor organoid tissue with a small molecule or agonist. In some embodiments, the small molecule or agonist that activates the TGFβ signaling pathway is TGFβ1. In some embodiments, the small molecule or agonist that activates the TGFβ signaling pathway is TGFβ1, TGFβ2, or TGFβ3.

In some embodiments, the methods further comprise culturing the obtained functional basal-like cells with FGF10 and Y27632. In some embodiments, the methods comprise culturing the stem cell-derived lung bud tip progenitor organoid tissue to obtain functional basal-like cells, and culturing the obtained functional basal-like cells with FGF10, Y27632, and one or more inhibitors of SMAD signaling (e.g., an inhibitor of the TGFβ signaling pathway and an inhibitor of the BMP signaling pathway).

Such embodiments are not limited to a specific TGFβ signaling pathway inhibitor. A TGF-β inhibitor (e.g., a small molecule or antagonist that inhibits the TGF-β signaling pathway) refers to inhibition of at least one of the proteins involved in the signal transduction pathway for TGF-β. It is contemplated herein that an inhibitor of the TGF-β signaling pathway can be, for example, a TGF-β receptor inhibitor (e.g., a small molecule, an antibody, an siRNA), a TGF-β sequestrant (e.g., an antibody, a binding protein), an inhibitor of receptor phosphorylation, an inhibitor of a SMAD protein, or a combination of such agents.

In some embodiments, the TGF-β signaling pathway inhibitor comprises or consists essentially of a TGF-β receptor inhibitor. One of skill in the art can easily test a compound to determine if it inhibits TGF-β receptor signaling by assessing, for example, phosphorylation status of the receptor or expression of downstream proteins controlled by TGF-β in cultured cells and comparing the results to cells not treated with a TGF-β receptor inhibitor. An agent is determined to be a TGF-β signaling pathway inhibitor if the level of phosphorylation of the Type I TGF-β receptor in a culture of cells is reduced by at least 20% compared to the level of phosphorylation of the Type I TGF-β receptor in cells that are cultured in the absence of a TGF-β signaling pathway inhibitor; preferably the level of phosphorylation is reduced by at least 30%, at least 40%, at least 50%, at least 60%, at least 70%, at least 80%, at least 90%, at least 95%, at least 99%, or even 100% (no phosphorylation) in the presence of a TGF-β signaling pathway inhibitor.

In some embodiments, the TGFβ signaling pathway inhibitor is A8308. In some embodiments, a TGF-β signaling pathway inhibitor is 513431542.

Such embodiments are not limited to a specific BMP signaling pathway inhibitor. In some embodiments, selective inhibiting of the BMP signaling pathway is accomplished with a small molecule or antagonist that inhibits the BMP signaling pathway. BMPs bind as a dimeric ligand to a receptor complex consisting of two different receptor serine/threonine kinases, type I and type II receptors. The type II receptor phosphorylates the type I receptor, resulting in the activation of this receptor kinase. The type I receptor subsequently phosphorylates specific receptor substrates (SMAD), resulting in a signal transduction pathway leading to transcriptional activity.

A BMP inhibitor (e.g., a small molecule or antagonist that inhibits the BMP signaling pathway) is defined as an agent that binds to a BMP molecule to form a complex wherein the BMP activity is neutralized, for example by preventing or inhibiting the binding of the BMP molecule to a BMP receptor. Alternatively, said inhibitor is an agent that acts as an antagonist or reverse agonist. This type of inhibitor binds with a BMP receptor and prevents binding of a BMP to said receptor. An example of a latter agent is an antibody that binds a BMP receptor and prevents binding of BMP to the antibody-bound receptor.

Several classes of natural BMP-binding proteins are known, including Noggin (Peprotech), Chordin and chordin-like proteins (R&D systems) comprising chordin domains, Follistatin and follistatin-related proteins (R&D systems) comprising a follistatin domain, DAN and DAN-like proteins (R&D systems) comprising a DAN cysteine-knot domain, sclerostin/SOST (R&D systems), decorin (R&D systems), and alpha-2 macroglobulin (R&D systems).

In some embodiments, the BMP inhibitor is Noggin.

In some embodiments, culturing the obtained functional basal-like cells with FGF10, Y27632, and one or more inhibitors of SMAD signaling (e.g., an inhibitor of the TGFβ signaling pathway and an inhibitor of the BMP signaling pathway) (e.g., A8308 and Noggin) occurs over a specified temporal period.

In some embodiments, culturing the obtained functional basal-like cells with FGF10, Y27632, and one or more inhibitors of SMAD signaling (e.g., an inhibitor of TGFβ1 and/or the TGFβ signaling pathway and an inhibitor of BMP4 and/or the BMP signaling pathway) (e.g., A8308 and Noggin) occurs simultaneously or does not occur simultaneously.

In some embodiments, the obtained functional basal-like cells are treated with the one or more SMAD signaling pathway inhibitors (e.g., A8308 and Noggin) and/or FGF10 and/or Y27632 for 6 or more hours; 12 or more hours; 18 or more hours; 24 or more hours; 36 or more hours; 48 or more hours; 60 or more hours; 72 or more hours; 84 or more hours; 96 or more hours; 120 or more hours; 150 or more hours; 180 or more hours; or 240 or more hours.

In some embodiments, the obtained functional basal-like cells are treated with the one or more SMAD signaling pathway inhibitors (e.g., Noggin and A8308) and/or the additional growth factors (e.g., FGF10 and/or Y27632) at a concentration of 10 ng/ml or higher; 20 ng/ml or higher; 50 ng/ml or higher; 75 ng/ml or higher; 100 ng/ml or higher; 120 ng/ml or higher; 150 ng/ml or higher; 200 ng/ml or higher; 500 ng/ml or higher; 1,000 ng/ml or higher; 1,200 ng/ml or higher; 1,500 ng/ml or higher; 2,000 ng/ml or higher; 5,000 ng/ml or higher; 7,000 ng/ml or higher; 10,000 ng/ml or higher; or 15,000 ng/ml or higher. In some embodiments, concentration of the one or more SMAD signaling pathway inhibitors, activators and/or additional growth factors is maintained at a constant level throughout the treatment. In other embodiments, concentration of the one or more SMAD signaling pathway inhibitors, activators and/or additional growth factors are varied during the course of the treatment. In some embodiments, the one or more SMAD signaling pathway inhibitors, activators and/or additional growth factors are suspended in media that include various concentrations of HyClone fetal bovine serine (FBS). One of skill in the art would understand that the regimen described herein is applicable to any known growth factors, alone or in combination. When two or more growth factors are used, the concentration of each growth factor may be varied independently.

In some embodiments, the obtained functional basal-like cells have one or more of the following characteristics: increased TP63 expression, increased KRT5 expression, increased KRT14 expression, increased EGFR expression, and increased F3 expression. In some embodiments, the obtained basal stem cells are capable of clonal expansion. In some embodiments, the obtained basal stem cells are capable of self-renewal. In some embodiments, the obtained basal stem cells are capable of multilineage differentiation.

In some embodiments, populations of cells enriched in pluripotent stem cell-derived lung bud tip progenitor organoid tissue are used. In some embodiments, the pluripotent stem cell-derived lung bud tip progenitor organoid tissue is isolated or substantially purified.

In some embodiments, functional basal-like cells produced in vitro from the described methods can be used to screen drugs for lung tissue uptake and mechanisms of transport. For example, this can be done in a high throughput manner to screen for the most readily absorbed drugs, and can augment Phase 1 clinical trials that are done to study drug lung tissue uptake and lung tissue toxicity. This includes pericellular and intracellular transport mechanisms of small molecules, peptides, metabolites, and salts.

In some embodiments, functional basal-like cells produced in vitro from the described methods can be used to identify the molecular basis of normal human lung development.

In some embodiments, functional basal-like cells produced in vitro from the described methods can be used to identify the molecular basis of congenital defects affecting human lung development.

In some embodiments, functional basal-like cells produced in vitro from the described methods can be used to correct lung related congenital defects caused by genetic mutations. In particular, mutations affecting human lung development can be corrected using iPSC technology and genetically normal functional basal-like cells produced in vitro from the described methods. In some embodiments, functional basal-like cells produced in vitro from the described methods can be used to generate replacement tissue.

In some embodiments, functional basal-like cells produced in vitro from the described methods can be used to generate replacement lung tissue for lung related disorders.

In some embodiments, a diagnostic kit or package is developed to include functional basal-like cells produced in vitro from the described methods and based on one or more of the aforementioned utilities.

EXAMPLES

The following examples are illustrative, but not limiting, of the compounds, compositions, and methods of the present invention. Other suitable modifications and adaptations of the variety of conditions and parameters normally encountered in clinical therapy and which are obvious to those skilled in the art are within the spirit and scope of the invention.

Example I

This example demonstrates that TGFβ1 and BMP4-mediated SMAD activation induces functional basal stem cells from fetal-lung and hPSC-derived bud tip progenitors in vitro.

Figure 1C:
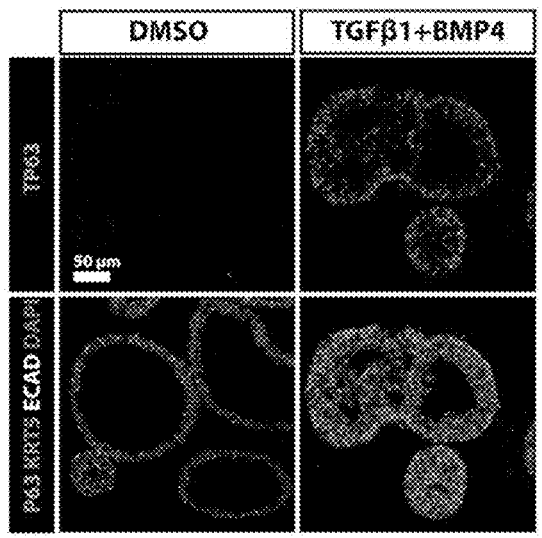
Figure 1D:
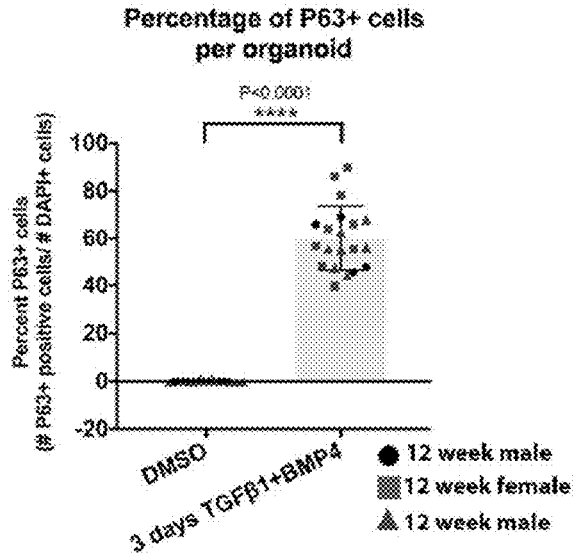
Figure 1E:
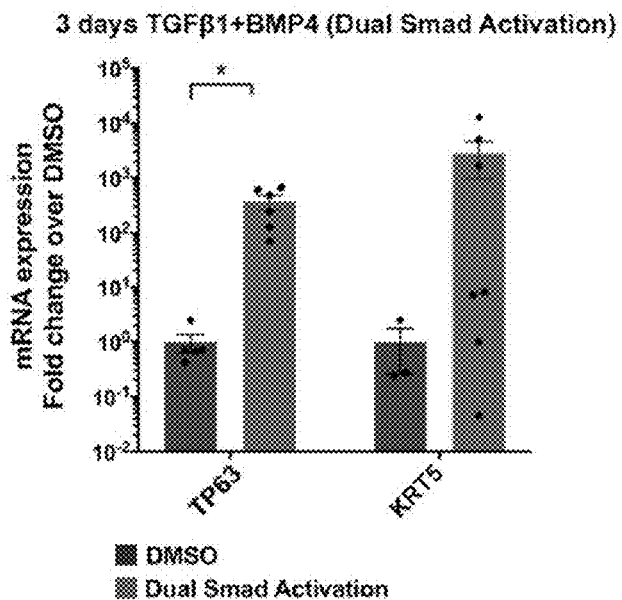
Figure 1F:
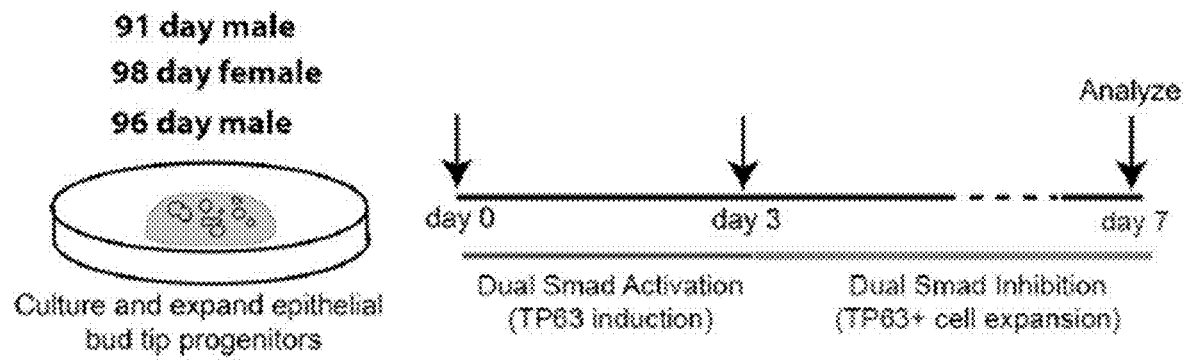
Figure 1G:
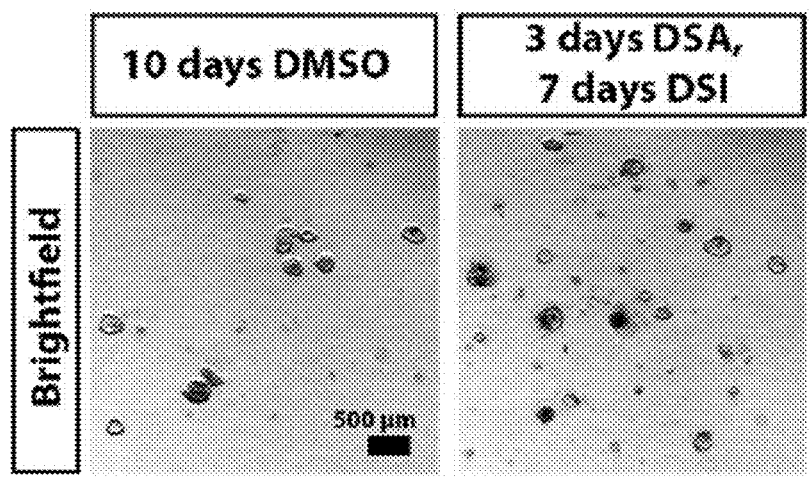
Figure 1H:
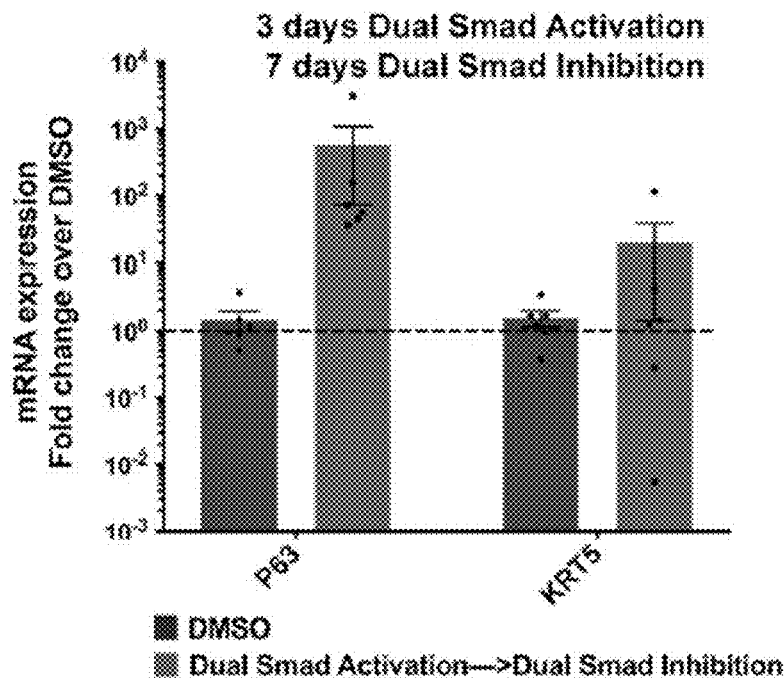
Figure 1I:
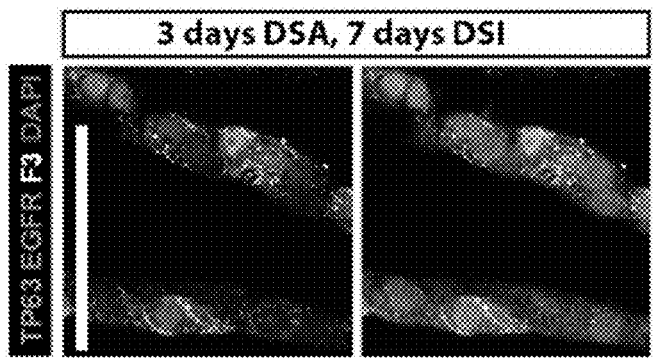
Figure 1J:
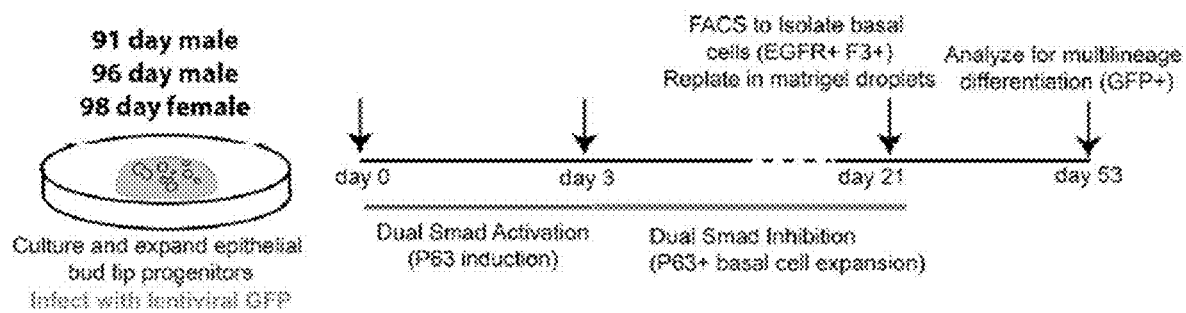
Figure 1K:
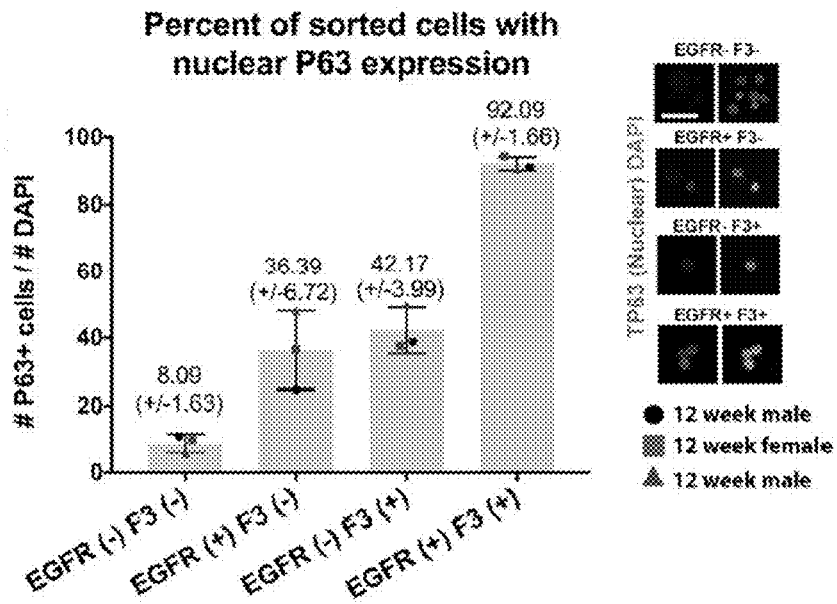
Figure 1L:
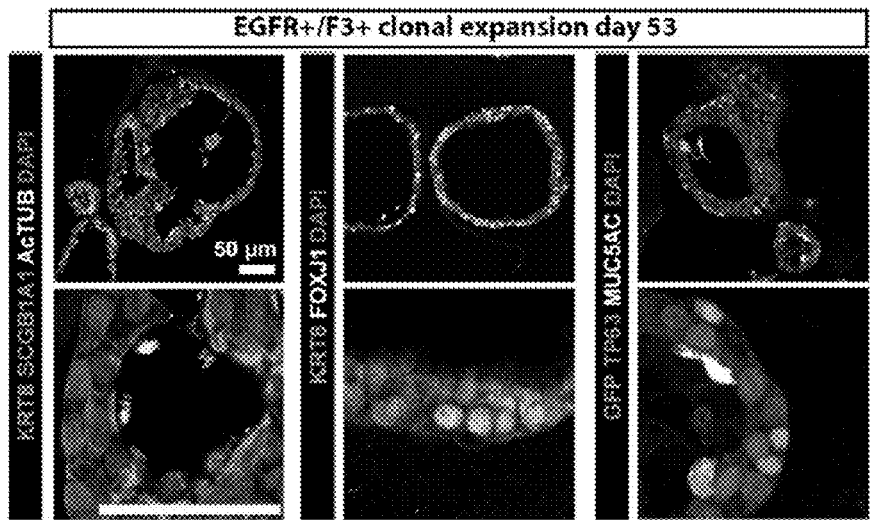
Figure 1M:
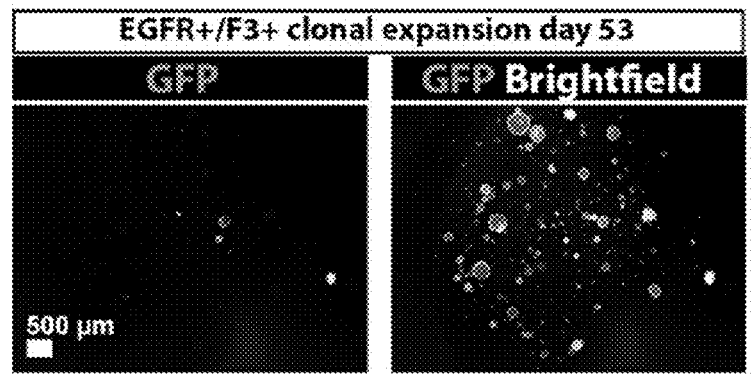
Figure 2A:
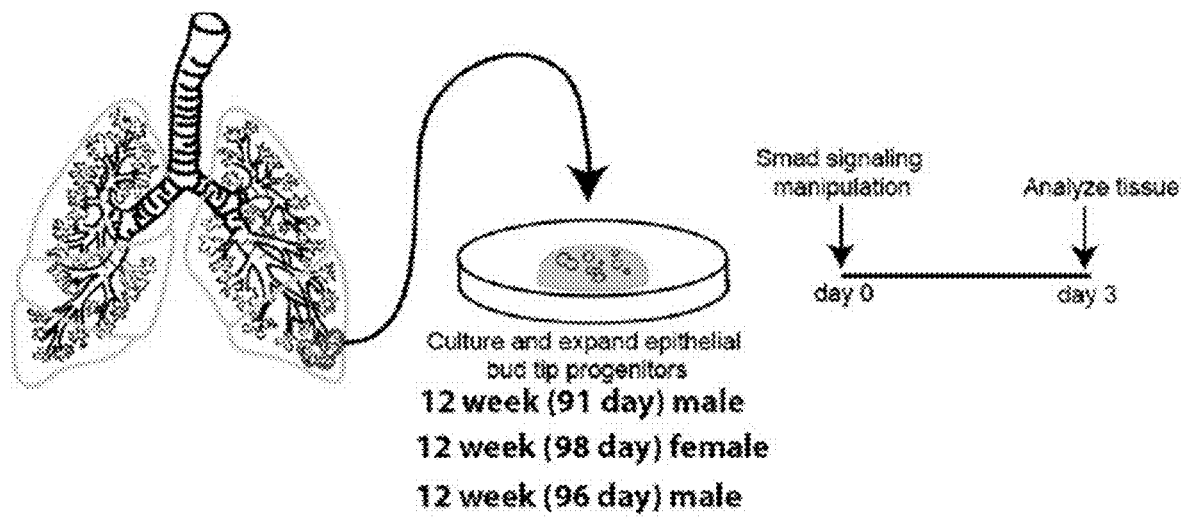
Figure 2B:
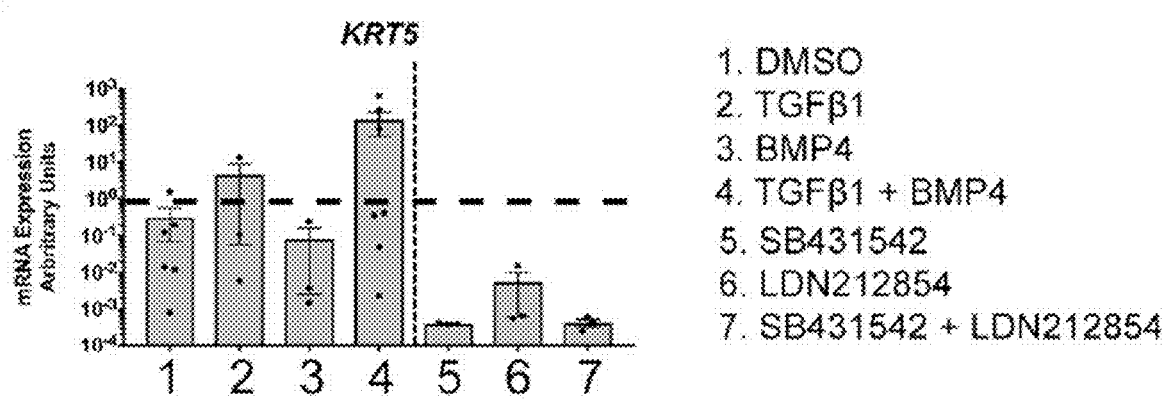
Figure 2C:
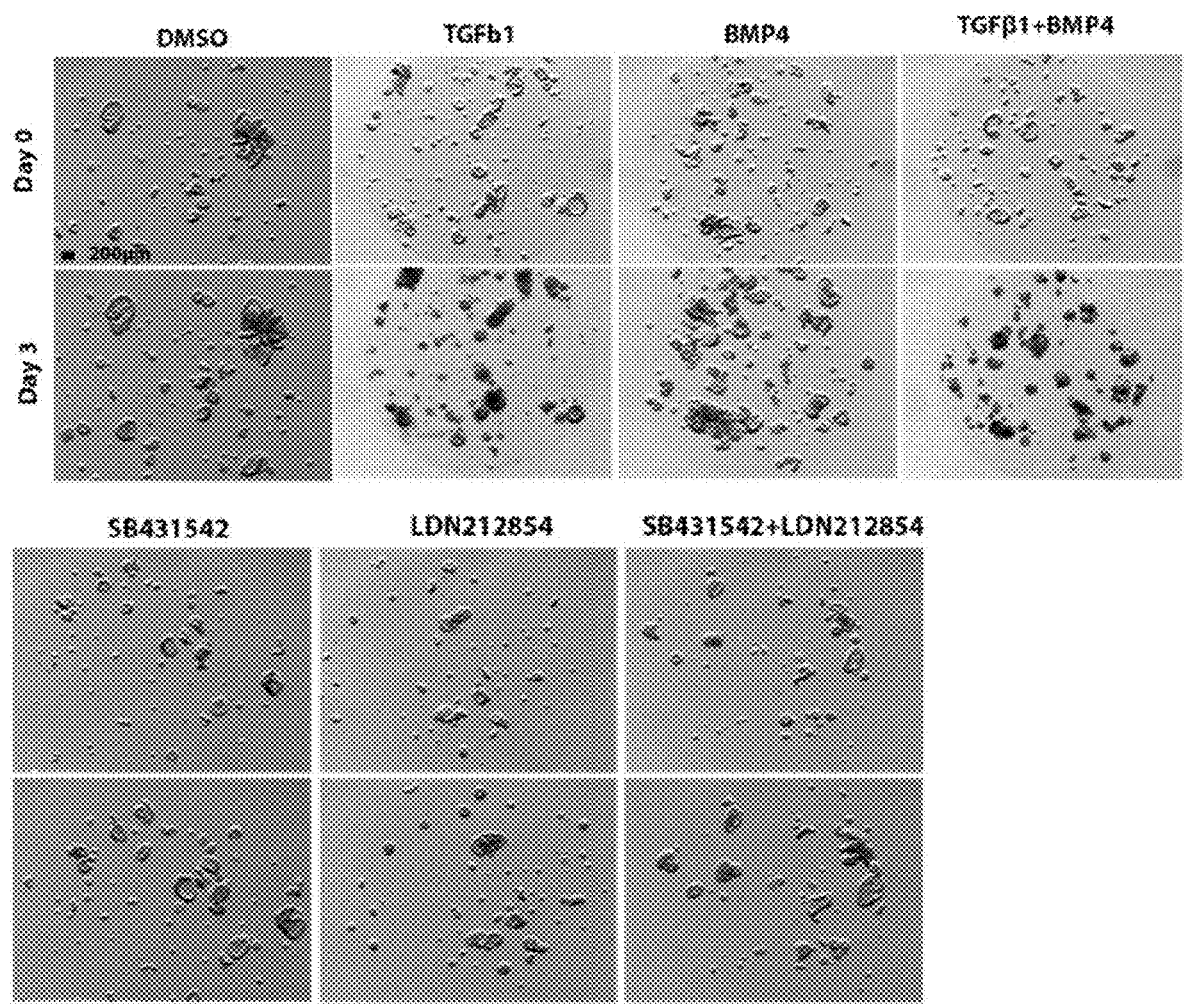
Figure 2D:
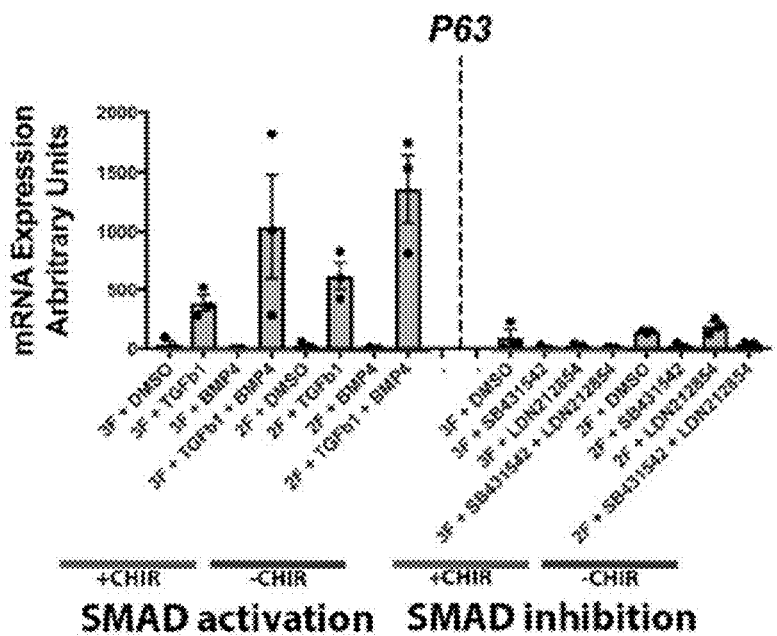
Figure 2E:
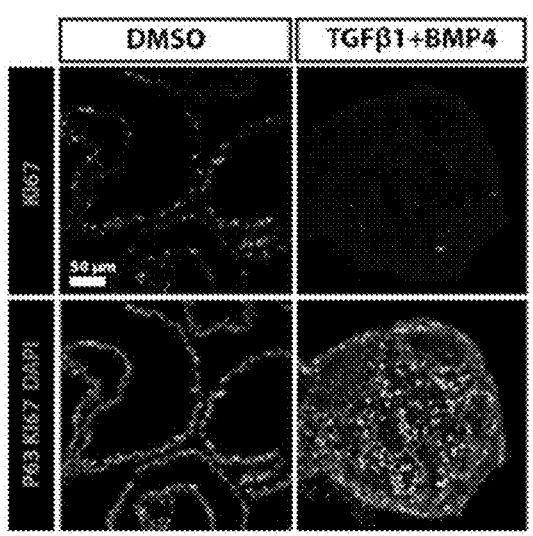
Figure 2F:
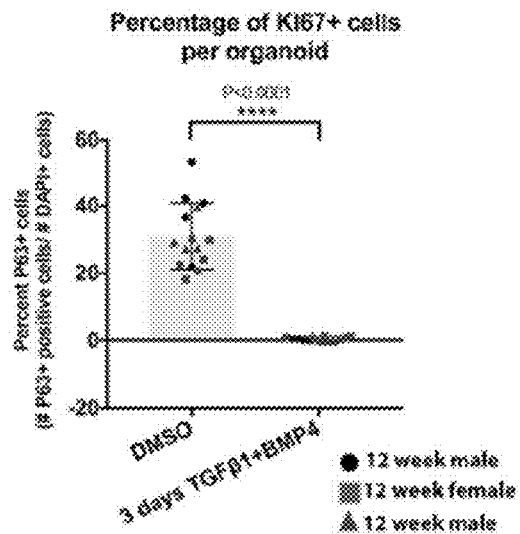

Experiments were conducted that utilized human fetal lung bud tip progenitor organoids isolated from 12 week fetal lungs (see, Miller A J, et al. (2018) Stem Cell Reports 10(1):101-119) and tested if activators or inhibitors of the TGFβ/BMP signaling pathways alone, or in combination, influenced TP63 expression (see, FIG. 1a-b, FIG. 2a-c, n=3). Supplementing normal progenitor organoid growth medium with TGFβ1 and BMP4 for 3 days (Dual SMAD Activation; DSA) led to the most significant increase in TP63 expression by QRT-PCR (FIG. 1b). 3 days of DSA also led to mRNA increases in KRT5 and KRT14, but showed no increase in markers for other lung epithelial cell types (FIG. 2i). DSA significantly increased TP63 expression both in the presence and absence of CHIR99021(FIG. 2d), a GSK3β inhibitor that is required to maintain bud tip organoids in their undifferentiated state (see, Miller A J, et al. (2018) Stem Cell Reports 10(1):101-119). Protein staining further revealed that 60.13% (+/−13.04%) of DSA treated bud tip organoid cells expressed TP63 after 3 days, compared to 0% in controls (FIG. 1c-d). DSA treatment led to more dense epithelial structures (FIG. 1c, FIG. 4c,e,g) with significantly reduced proliferation as measured by KI67 staining (FIG. 2e-f) and increased apoptosis (FIG. 2g-h). Consistent with mesenchyme-free organoid experiments, such experiments similarly found that explanted pieces of distal lung tissue (10-11 week fetal lung), which included epithelium plus mesenchyme grown in a serum free minimal media, treated with DSA led to a significant increase in TP63 protein and mRNA expression.

Figure 3A:
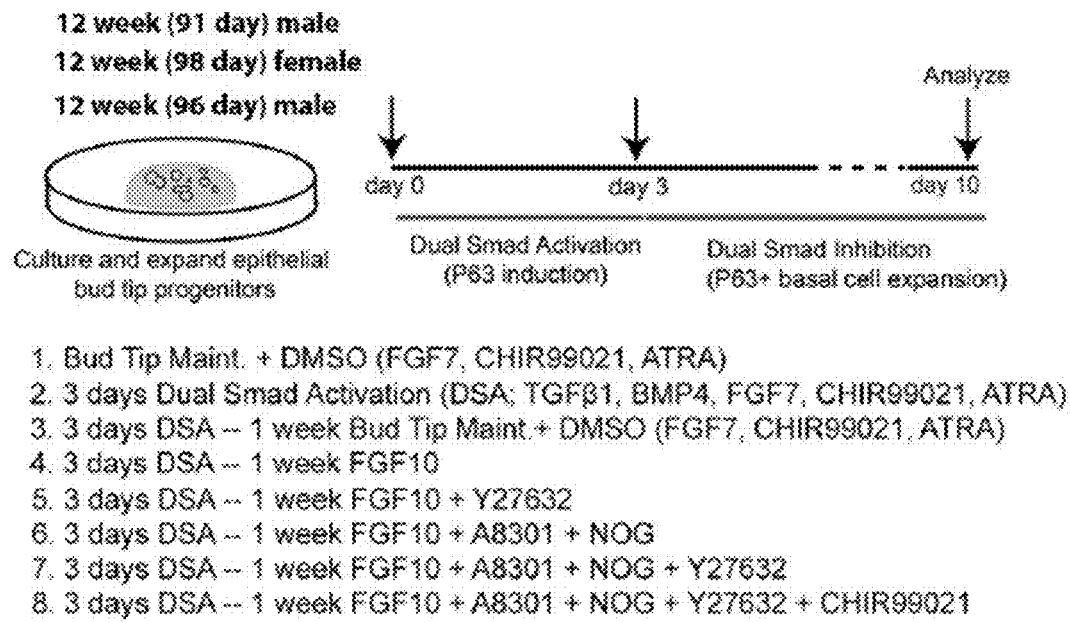
Figure 3B:
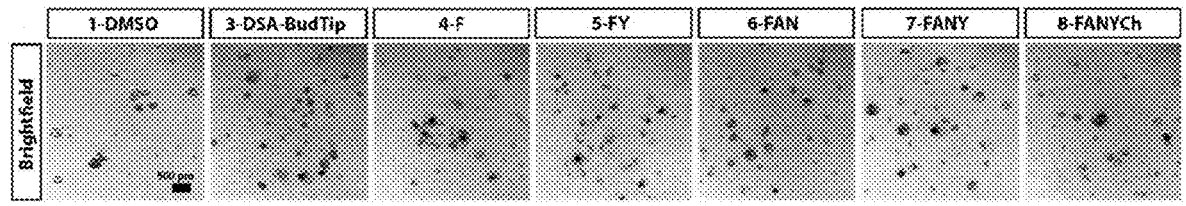
Figure 3C:
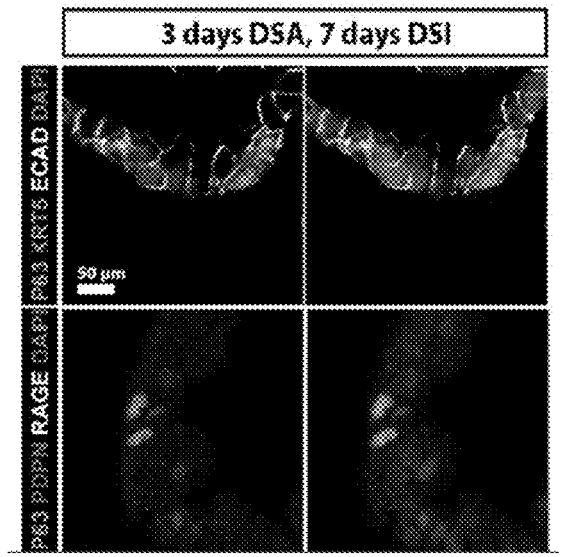
Figure 3D:
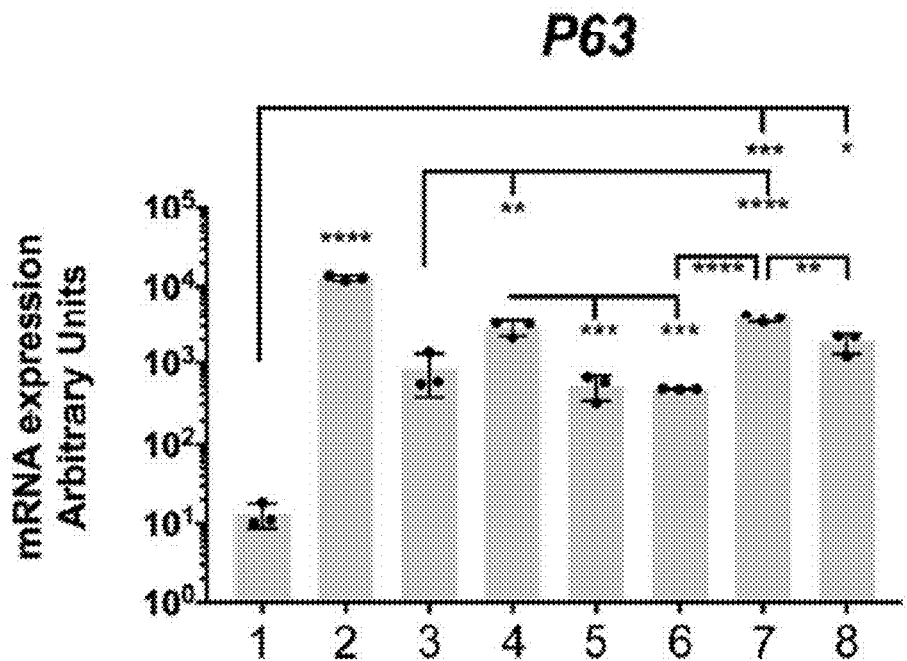
Figure 3E:
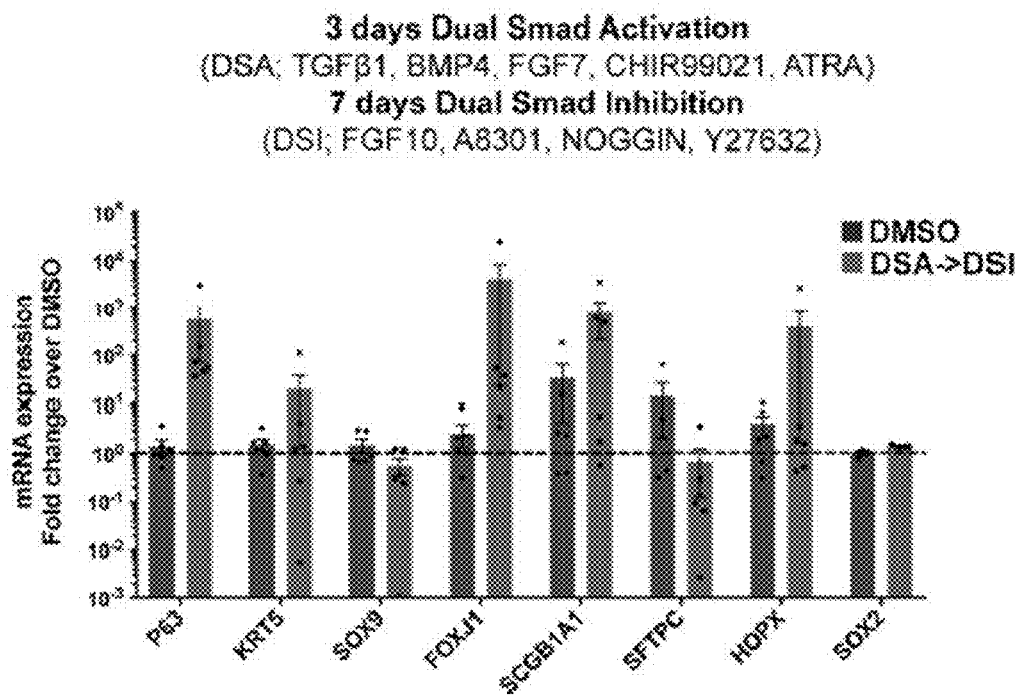
Figure 4A:
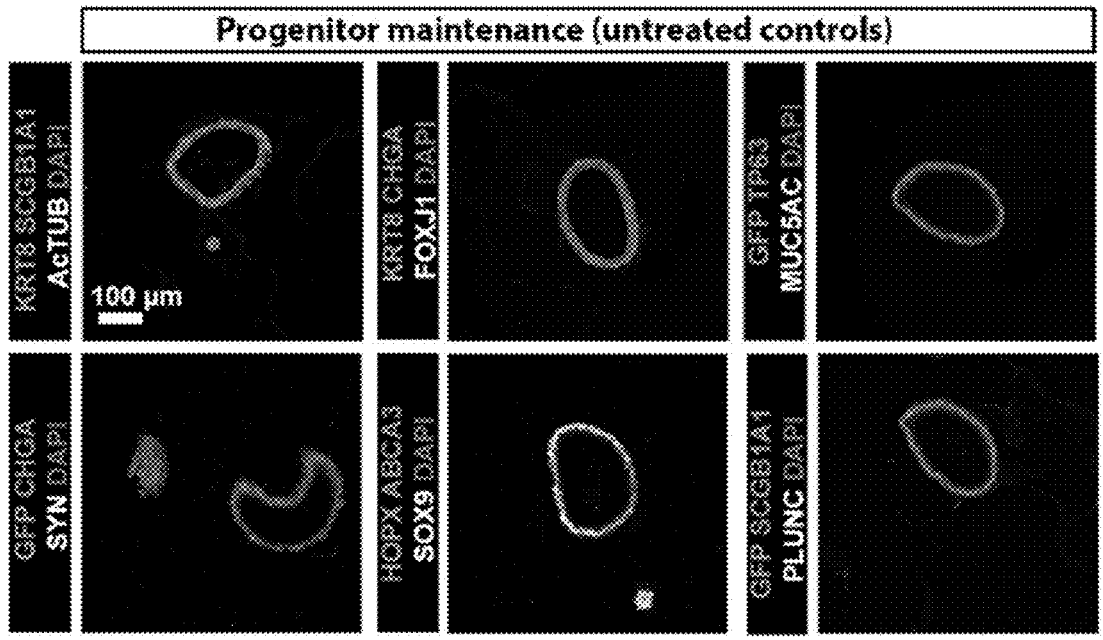
Figure 4B:
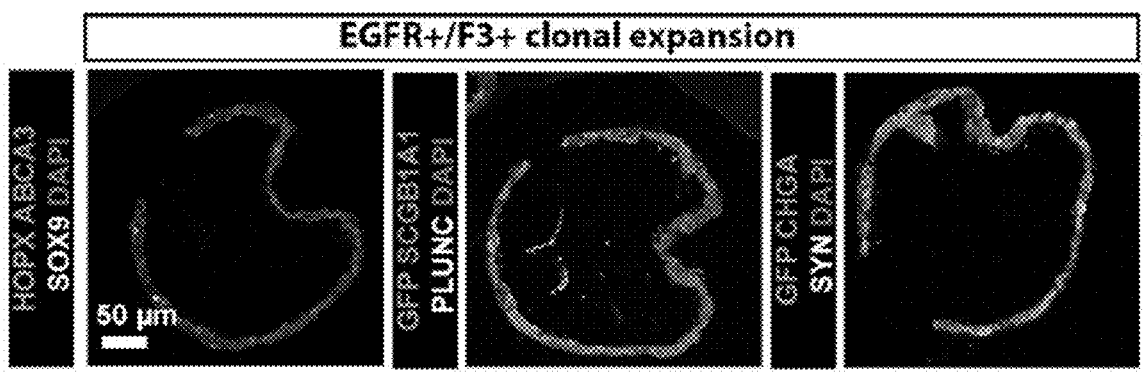
Figure 4C:
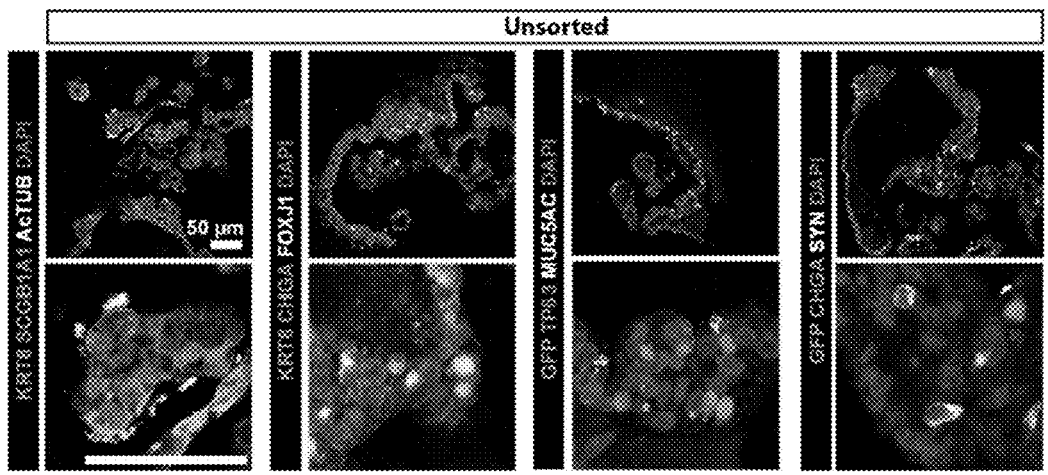
Figure 4D:
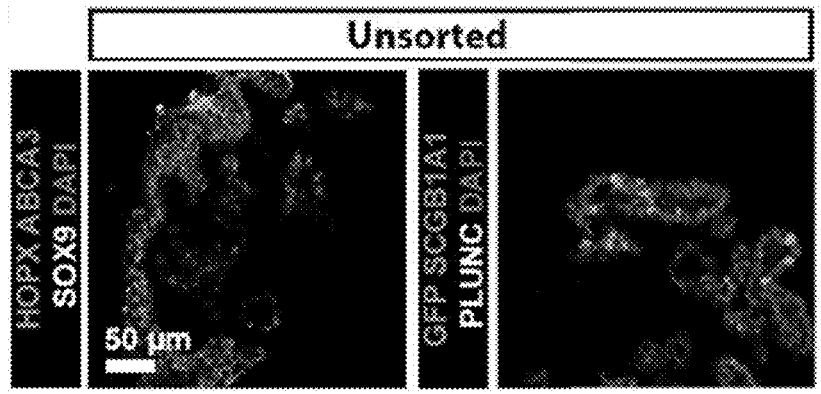

The findings show that TP63 is robustly induced in bud tip progenitor cells exposed to DSA but that prolonged treatment also blocked proliferation and induced cell death. Previous work in mice and humans has shown that inhibition of TGFβ/BMP (Dual SMAD Inhibition; DSI) is required for expansion of mature adult basal stem cells in culture (see, Mou H, et al. (2016) Cell Stem Cell. doi:10.1016/j.stem.2016.05.012; Tadokoro T, et al., (2016) Development 143(5):764-773). It was reasoned that while DSA is sufficient to induce TP63 expression, it may be detrimental to cell expansion, and so experiments were conducted that screened for growth factor conditions that allowed the DSA-induced cell population to expand in culture (FIG. 1f-i; FIG. 6a-d). It was found that DSI plus supplementation of the medium with FGF10 and Y27632, a ROCK kinase inhibitor ('DSI expansion medium': FGF10, A8308, NOGGIN, Y27632), promoted organoid survival and expansion, and was permissive for continued TP63 expression (FIG. 1g-i, FIG. 3a-e). DSI expansion medium is based on published reports demonstrating the importance of these factors for basal cell proliferation, survival and/or expansion (see, Mou H, et al. (2016) Cell Stem Cell. doi:10.1016/j.stem.2016.05.012; Tadokoro T, et al., (2016) Development 143(5):764-773; Balasooriya GI, et al., (2017) Development 144(9):1600-1606). Organoids grown in expansion medium also demonstrated increased mRNA and protein expression of markers canonically associated with multiciliated and club cell lineages (FOXJ1, SCGB1A1, respectively (FIG. 3e, FIG. 4c). Organoids grown in expansion medium contained TP63+ cells that co-expressed EGFR and F3 (FIG. 1i), which were identified as human fetal basal stem cell markers from scRNAseq analysis of human fetal tracheal epithelial cells. After several days in culture, many beating multiciliated cells were present within organoids and the proteinaceous luminal contents within organoids appeared to swirl with directionality, suggesting that multiciliated cells are functional and able to propel luminal contents.

Figure 4E:
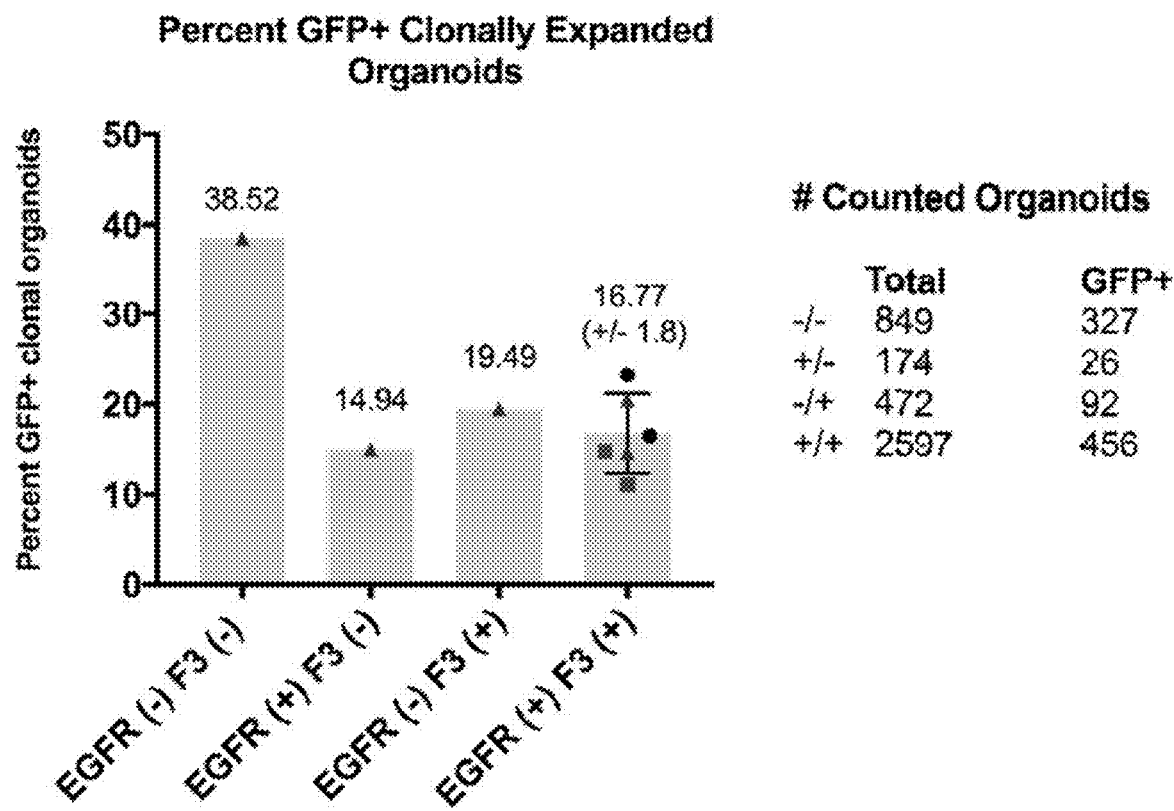
Figure 5A:
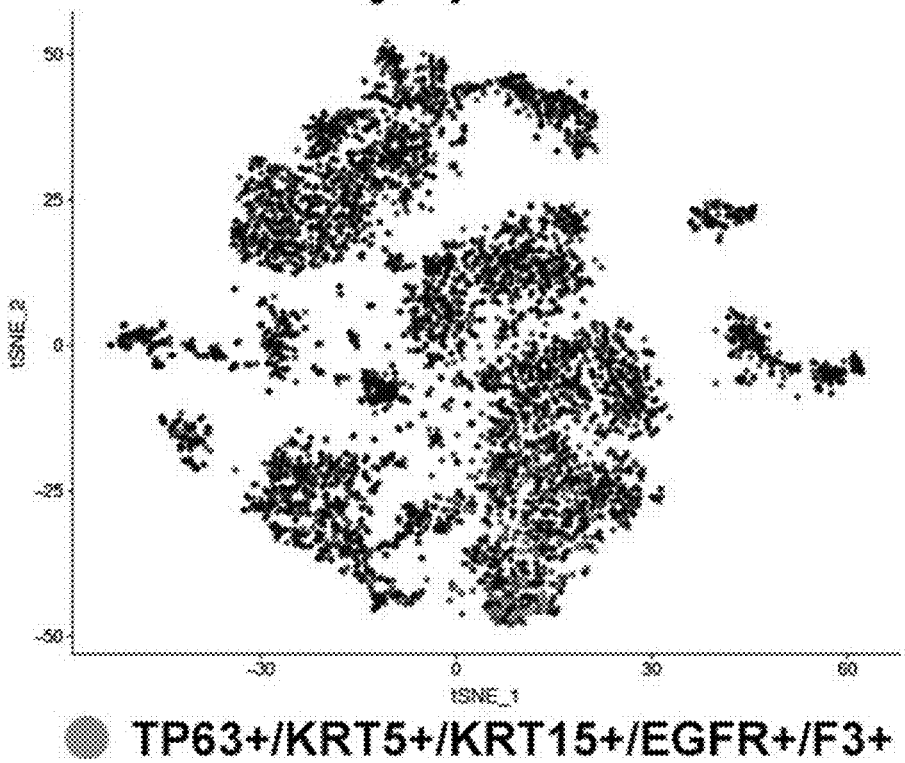
Figure 5B:
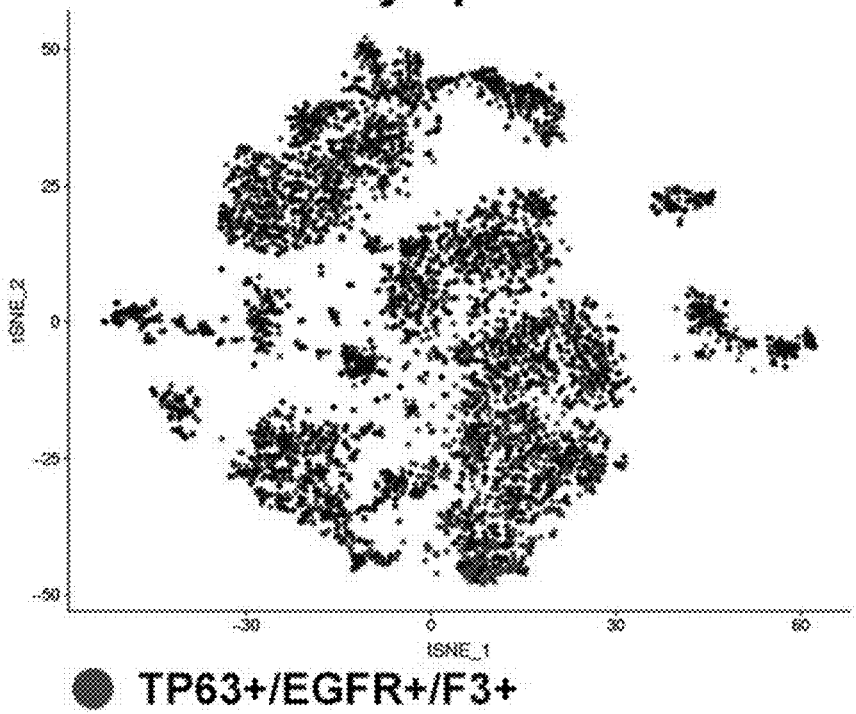
Figure 5C:
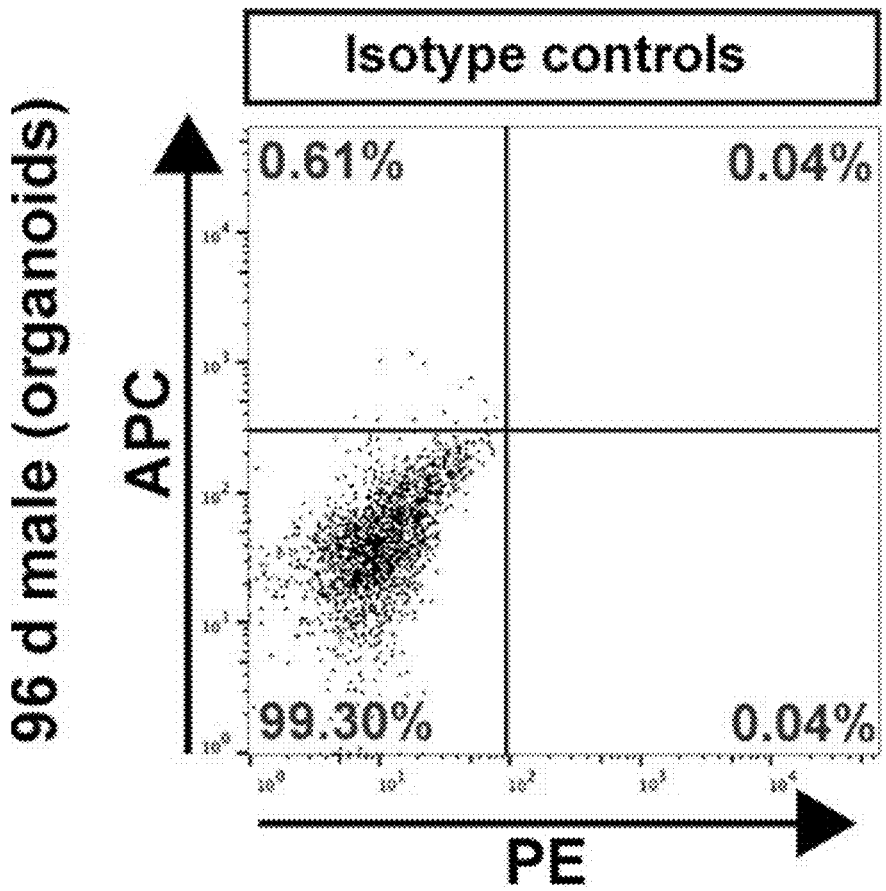
Figure 5D:
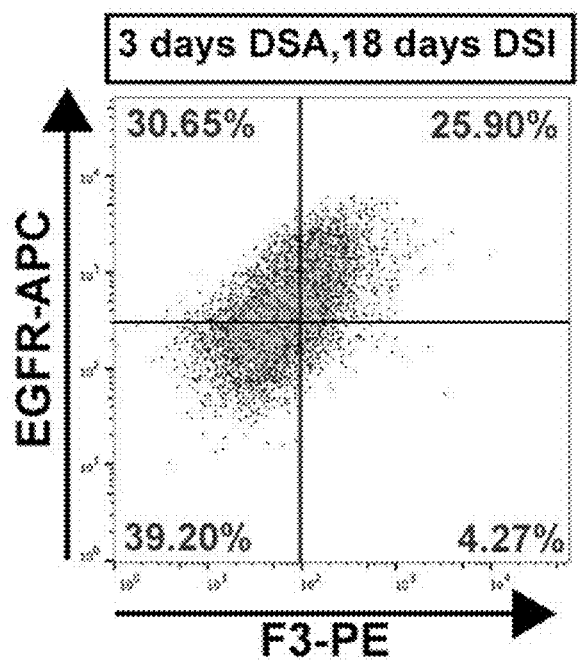

In order to determine if DSA-induced TP63+ cells have the capability for self-renewal and multi-lineage differentiation, experiments were conducted that isolated TP63+ cells with FACS using the basal cell enriched cell surface proteins EGFR and F3 (FIG. 1, FIG. 5a-b). Prior to DSA induction, bud tip organoids were infected with a lentivirus to drive constitutive GFP expression in a random subset of cells (~20%, FIG. 3l) in order to track and visualize these cells over time. Bud tip organoids were then treated with DSA for 3 days to induce TP63 expression, and expanded for 18 days in expansion media (FIG. 1j). Organoids were subsequently dissociated and FACS was used to isolate EGFR+/F3+ cells (FIG. 1j, FIG. 5f-1). FACS isolated cells were immediately affixed to slides via cytospinning and were stained for TP63 protein. This analysis showed that 92.09 (+/−1.66)% of EGFR+/F3+ cells co-expressed nuclear TP63 whereas EGFR+/F3−, EGFR−/F3+ or EGFR−/F3− fractions had a far lower proportion of cells that expressed TP63 (FIG. 1k, n=3). After sorting, EGFR+/F3+ cells were replated and grown in vitro, where approximately 15-30% of all organoids across groups were GFP+. It was also noted that and organoids were either GFP+ or GFP−, but were not mixed, suggesting that individual organoids were derived from clonal expansion, rather than from cell aggregation (FIG. 1m, FIGS. 4e and 10l). Clonally expanded EGFR+/F3+ cells gave rise to TP63+ basal, MUC5AC+ goblet, SCGB1A1+ club and AcTUB+/FOXJ1+ multiciliated cells as shown by protein staining (FIG. 1l), and clonally expanded GFP+ organoids exhibited multiciliated cells that were observed to beat, along with swirling luminal mucous. Together, this data indicates that DSA induces a population of functional basal-like cells from bud tip progenitor organoids in vitro.

Repetition of these experiments with hPSCs and iPSCs-derived bud tip progenitor organoids (see, Miller A J, et al. (2018) Stem Cell Reports 10(1):101-119) showed that treatment with progenitor maintenance medium plus DSA led to a drastic increase in the number of TP63+ cells compared to DMSO controls (FIG. 6b) and a statistically significant increase in mRNA expression of TP63 by QRT-PCR (FIG. 6c). After 45 days in culture, organoids contained many TP63+ cells in addition to multiciliated (AcTUB, white) and mucous producing cells (SCGB1A1, pink; FIG. 6d).

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

Incorporation by Reference

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

We claim:

1. A method, comprising:
   (i) differentiating human fetal lung bud tip progenitor organoids comprising $Sox2^+/Sox9^+$ cells into organoids comprising cells expressing TP63, wherein the differentiating comprises contacting the human fetal lung bud tip progenitor organoids comprising $Sox2^+/Sox9^+$ cells in vitro with a composition comprising TGF-β and BMP4 to obtain organoids comprising cells expressing TP63; and
   (ii) expanding the organoids comprising cells expressing TP63, wherein the expanding comprises contacting the organoids comprising cells expressing TP63 with a composition comprising FGF10, Y27632, A8301, and Noggin;
   wherein the cells expressing TP63 further express one or more of KRT5, KRT14, and F3;
   wherein the expanded organoids comprising cells expressing TP63 are capable of clonal expansion, self-renewal and multilineage differentiation.

* * * * *